United States Patent
Irla

(10) Patent No.: US 12,325,735 B2
(45) Date of Patent: *Jun. 10, 2025

(54) REGULATORY T CELLS GENETICALLY MODIFIED FOR THE LYMPHOTOXIN ALPHA GENE AND USES THEREOF

(71) Applicants: INSERM (INSTITUT NATIONAL DE LA SANTÉ ET DE LA RECHERCHE MÉDICALE), Paris (FR); UNIVERSITÉ D'AIX MARSEILLE, Marseilles (FR); CENTRE NATIONAL DE LA RECHERCHE SCIENTIFIQUE (CNRS), Paris (FR)

(72) Inventor: Magali Irla, Marseilles (FR)

(73) Assignees: INSERM (INSTITUT NATIONAL DE LA SANTE ET DE LA RECHERCHE MEDICALE), Paris (FR); UNIVERSITE D'AIX-MARSEILLE, Marseilles (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/168,114

(22) Filed: Feb. 13, 2023

(65) Prior Publication Data
US 2023/0272342 A1    Aug. 31, 2023

Related U.S. Application Data

(62) Division of application No. 16/763,020, filed as application No. PCT/EP2018/081078 on Nov. 13, 2018, now Pat. No. 11,618,884.

(30) Foreign Application Priority Data

Nov. 14, 2017 (EP) ..................... 17306579

(51) Int. Cl.
*C07K 14/705* (2006.01)
*A61K 35/12* (2015.01)
*A61K 39/00* (2006.01)
*A61K 40/11* (2025.01)
*A61K 40/22* (2025.01)
*A61K 40/41* (2025.01)
*A61P 35/00* (2006.01)
*C12N 5/0783* (2010.01)

(52) U.S. Cl.
CPC ........ *C07K 14/70596* (2013.01); *A61K 40/11* (2025.01); *A61K 40/22* (2025.01); *A61K 40/416* (2025.01); *A61P 35/00* (2018.01); *C12N 5/0637* (2013.01); *A61K 2035/122* (2013.01); *A61K 2239/31* (2023.05); *A61K 2239/38* (2023.05)

(58) Field of Classification Search
None
See application file for complete search history.

(56) References Cited

U.S. PATENT DOCUMENTS 11,618,884 B2 * 4/2023 Irla ..................... C12N 5/0637
424/93.71

OTHER PUBLICATIONS

Brinkman, 2016, Nature Communications, pp. 1-16.*
Piao, 2020, Cell Rep. vol. 30: 1052-1062.*

* cited by examiner

*Primary Examiner* — Amy E Juedes
(74) *Attorney, Agent, or Firm* — WCF IP

(57) ABSTRACT

The present invention relates to regulatory T cell and uses thereof. By their immunosuppressive and anti-inflammatory activities, regulatory T cells play a central role in peripheral tolerance and thus critically prevent the development of autoimmune and inflammatory disorders. The inventors showed that Foxp3+CD4+ Tregs express high levels of LTα, which negatively regulates their immunosuppressive signature. They demonstrated that the adoptive transfer of LTα−/− Tregs in mice protects from dextran sodium sulfate (DSS)-induced colitis and attenuates inflammatory bowel disease (IBD), multi-organ autoimmunity and the development of CAC. The inventors also showed that by mixed bone marrow chimeras that LTα expression specifically in hematopoietic cells negatively controls the immunosuppressive signature of Tregs. In particular, the present invention relates to regulatory T cell characterized in that it does not express or expresses reduced levels of lymphotoxin alpha.

2 Claims, 19 Drawing Sheets

Figure 1A:
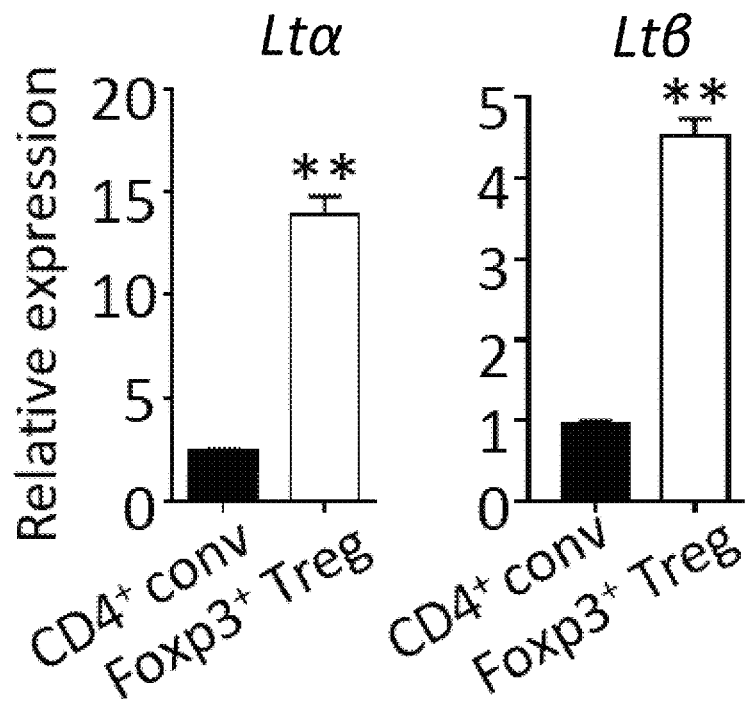

REGULATORY T CELLS GENETICALLY MODIFIED FOR THE LYMPHOTOXIN ALPHA GENE AND USES THEREOF

FIELD OF THE INVENTION

The present invention relates to regulatory T cell and uses thereof. More particularly, the present invention relates to regulatory T cell characterized in that it does not express lymphotoxin alpha or expresses reduced levels of lymphotoxin alpha and their use for the treatment and prevention of autoimmune disorders and inflammatory-associated cancers.

BACKGROUND OF THE INVENTION

CD4+CD25+Foxp3+ regulatory T cells (Tregs) constitute a subset of CD4+ T cells that plays a critical role in the maintenance of peripheral self-tolerance (Sakaguchi, S., et al. (2008). Regulatory T cells and immune tolerance. Cell 133, 775-787). This cell type possesses the unique ability to immunosuppress hazardous autoreactive T cells that have escaped thymic negative selection and thereby prevents the development of inflammatory and autoimmune disorders. Foxp3+ Treg cells originate from both the thymus and the conversion of naïve CD4+ T cells in the periphery and are called natural and induced Tregs, respectively (Dhamne, C. et al. (2013). Peripheral and thymic foxp3(+) regulatory T cells in search of origin, distinction, and function. Front Immunol 4, 253). During ontogeny, the development of natural Tregs is substantially delayed compared to that of conventional CD4+ T cells since the first wave of Tregs is generated during the perinatal period whereas conventional CD4+ T cells appear earlier at the embryonic stage (Fontenot, J. D. et al. (2005). Developmental regulation of Foxp3 expression during ontogeny. The Journal of experimental medicine 202, 901-906).

The importance of Foxp3+ Treg cells in the control and maintenance of our immune system was illustrated with scurfy mice that show a mutation in the Foxp3 gene resulting in a truncated non-functional Foxp3 protein (Brunkow, M. E. et al. (2001). Disruption of a new forkhead/winged-helix protein, scurfin, results in the fatal lymphoproliferative disorder of the scurfy mouse. Nature genetics 27, 68-73). These mice die at an early age because they fail to produce thymic-derived Foxp3+ Tregs and thus develop a fatal lymphoproliferative syndrome with multi-organ inflammation. Foxp3 was subsequently identified as the master regulator of Treg development, function and homeostasis. Genetic mutations in the Foxp3 gene have also been identified in humans and are responsible of a severe autoimmune disorder called Immune dysregulation Polyendocrinopathy Enteropathy X-linked (IPEX) syndrome (Bennett, C. L. et al. (2001). The immune dysregulation, polyendocrinopathy, enteropathy, X-linked syndrome (IPEX) is caused by mutations of FOXP3. Nature genetics 27, 20-21).

Foxp3+ Tregs use several mechanisms to suppress the immune response (Workman et al., 2009). Four main modes of action have been described: immunosuppressive cytokines (IL-10, TGF-β and IL-35), cytolysis of effector T cells and dendritic cells (Granzyme B and A in mice and humans, respectively), metabolic disruption (CD39, CD73 and CD25) and the modulation of antigen presentation in dendritic cells (CTLA-4 and LAG-3).

In mice, the adoptive transfer of WT Tregs in inflammatory bowel disease (IBD) has been shown to prevent and cure established intestinal inflammation (Maloy, K. J. et al. (2003). CD4+CD25+T(R) cells suppress innate immune pathology through cytokine-dependent mechanisms. The Journal of experimental medicine 197, 111-119), type I diabetes (Szanya, V. et al. (2002). The subpopulation of CD4+CD25+ splenocytes that delays adoptive transfer of diabetes expresses L-selectin and high levels of CCR7. Journal of immunology 169, 2461-2465), experimental autoimmune encephalomyelitis (EAE) (McGeachy, M. J. et al. (2005). Natural recovery and protection from autoimmune encephalomyelitis: contribution of CD4+CD25+ regulatory cells within the central nervous system. Journal of immunology 175, 3025-3032), and asthma (Presser, K. et al. (2008). Coexpression of TGF-beta1 and IL-10 enables regulatory T cells to completely suppress airway hyperreactivity. Journal of immunology 181, 7751-7758). Furthermore, while Treg cells are often protumoral by attenuating tumor immunosurveillance, they in contrast play an antitumoral role in chronic inflammation-mediated cancers by dampening inflammation such as in colitis-associated cancer (CAC) (Waldner, M. J., and Neurath, M. F. (2009). Colitis-associated cancer: the role of T cells in tumor development. Semin Immunopathol 31, 249-256). In humans, Treg-based cellular therapy is becoming a reality (Riley, J. L. at al. (2009). Human T regulatory cell therapy: take a billion or so and call me in the morning. Immunity 30, 656-665). For example, phase 1 clinical trials using human Tregs have been reported in patients suffering from type I diabetes (Bluestone, J. A., et al. (2015). Type 1 diabetes immunotherapy using polyclonal regulatory T cells. Sci Transl Med 7), refractory Crohn's disease (Desreumaux, P. et al. (2012). Safety and efficacy of antigen-specific regulatory T-cell therapy for patients with refractory Crohn's disease. Gastroenterology 143) or acute graft versus host disease (GVHD) upon stem cell transplantation (Di Ianni, M. et al. (2011). Tregs prevent GVHD and promote immune reconstitution in HLA-haploidentical transplantation. Blood 117, 3921-3928). However, it still a need for developing autoimmune and inflammatory diseases new therapies.

Additionally, it exists a major limiting step on the Treg adoptive transfer technique: a large quantity of cells is required for effective therapy in human. Thus, in the field of Treg cell therapy, it still a need for reducing the required cell numbers to treat efficiently inflammatory and autoimmune disorders.

SUMMARY OF THE INVENTION

The present invention relates to regulatory T cells and uses thereof. More particularly, the present invention relates to regulatory T cell characterized in that it does not express lymphotoxin alpha or expresses reduced levels of lymphotoxin alpha and their use for the treatment and prevention of autoimmune disorders and inflammatory-associated cancers. In particular, the invention is defined by the claims.

DETAILED DESCRIPTION OF THE INVENTION

By their immunosuppressive and anti-inflammatory activities, Foxp3+CD4+ regulatory T cells (Tregs) play a central role in peripheral tolerance and thus critically prevent the development of autoimmune and inflammatory disorders. The inventors showed that thymic and splenic Foxp3+CD4+ Tregs express higher levels of lymphotoxin a (LTα) than conventional CD4+ T cells, as a membrane anchored LTα1β2 heterocomplex. Importantly, this expression in Foxp3+CD4+ Tregs is conserved in human. Thymic and splenic Foxp3+CD4+ Tregs from LTα−/− mice (LTα−/−

Tregs) exhibit a signature of highly suppressive cells, indicating that LTα negatively regulates the immunosuppressive functions of this cell type.

Interestingly, by limiting bowel inflammation, the adoptive transfer (AT) of LTα−/− Tregs protects from dextran sodium sulfate (DSS)-induced colitis, cures inflammatory bowel disease (IBD) and attenuates the development of colitis-associated cancer (CAC). The AT of LTα−/− Tregs also attenuates the severity of multi-organ autoimmunity. Furthermore, the administration of four times less LTα−/− Treg cell shows the same protection than WT Tregs against DSS-induced colitis. High-throughput RNA-seq revealed that LTα−/− Tregs adopt specialized differentiation programs and thus exhibit an activated/effector phenotype. Importantly, mixed bone marrow chimeras revealed that LTα expression specifically in hematopoietic cells negatively controls the suppressive signature of Tregs.

Finally, they also demonstrated that LTα1β2/LTβR interactions between Tregs and antigen presenting cells (i.e. dendritic cells and thymic epithelial cells) respectively control the immunosuppressive signature of Tregs.

Altogether, their findings thus identified that LTα negatively regulates the immunosuppressive properties of Tregs and thus could constitute a valuable new target in therapy to increase Treg suppressive activities. Moreover, by increasing the immunosuppressive activity of Tregs, the number of cells to be injected in adoptive transfer may be reduced, which represents a technical facilitation.

Regulatory T Cells of the Invention

Accordingly, a first aspect of the present invention relates to a regulatory T cell characterized in that it does not express or expresses reduced levels of lymphotoxin alpha. This permits to increase the suppressive activity of regulatory T cells.

In one embodiment, the gene coding for lymphotoxin alpha is deleted.

In one embodiment, the gene coding for lymphotoxin alpha is mutated resulting on a non-viable RNA.

As used herein, the term "regulatory T cells" or "Tregs" refers to a subpopulation of T cells which modulates the immune system, maintains tolerance to self-antigens, and abrogates autoimmune and inflammatory diseases. These cells generally suppress or downregulate induction and proliferation of effector T cells and modulate antigen presenting cell function. Tregs are cells capable of suppressive activity (i.e. inhibiting proliferation of conventional T cells), either by cell-cell contact or through the release of immunosuppressive cytokines. As used herein, the term "lymphotoxin alpha" or "LT-α" (also known as tumor necrosis factor-beta (TNF-β)) refers to a member of the tumor necrosis factor family. Lymphotoxin alpha is a cytokine secreted by lymphocytes. Lymphotoxin alpha (Uniprot reference: P01374 for *Homo sapiens*, P09225 for *Mus musculus*) is encoded by the lymphotoxin alpha (LTA) gene (NCIBI reference: Gene ID: 4049 for *Homo sapiens*, Gene ID: 16992 for *Mus musculus*).

As used herein, the expression "expresses reduced levels of lymphotoxin alpha" means that the regulatory T cell expresses less lymphotoxin alpha compared to its wild type unmanipulated counterpart.

The term "gene" refers to a natural or synthetic polynucleotide containing at least one open reading frame that is capable of encoding a particular polypeptide or protein after being transcribed or translated.

As used herein the term "deleted" means a total or partial deletion of the gene. A partial deletion can involve the removal of any amount of DNA from the target gene, from 1 base pair (bp) up to almost the entire polypeptide coding region of the gene. A total deletion involves the removal of the entire coding region of the gene with or without flanking sequences, which may or may not include regulatory elements that are required for gene function, for example transcriptional promoters. Furthermore, the deletion may result in the removal of just a regulatory region, such as a promoter, leaving the coding region intact. The result is that no mRNA can be produced and so the gene is rendered defective.

In one embodiment, a small portion of the second exon, the entire third exon, and a small portion of the fourth exon of the gene encoding murine LT alpha with a neo cassette have been deleted in order to silence the LT alpha gene (as described in De Togni et al. Science. 1994 Apr. 29; 264 (5159):703-7).

As used herein, the term "mutated gene" as used herein means a gene in which a mutation has occurred. The term "mutation" as used herein means a change in the sequence of a nucleic acid and includes a base substitution, insertion, deletion, inversion, duplication, translocation, and the like used in genetics and the like. The region of the mutation in a mutated gene is not limited to a transcriptional region, but includes a regulatory region such as a promoter which is required for gene expression.

As used herein, the term "non-viable RNA" relates to a RNA which is not translated into protein.

Another object of the present invention relates to a population of regulatory T cells of the invention.

As used herein, the term "population" refers to a population of cells, wherein the majority (e.g., at least about 50%, preferably at least about 60%, more preferably at least about 70%, and even more preferably at least about 80%) of the total number of cells have the specified characteristics of the cells of interest and express the markers of interest.

Another object of the present invention relates to an ex vivo method for stimulating regulatory T cells immunosuppressive activity, said method comprising:
 i) Obtaining a biological sample from a subject;
 ii) Isolating regulatory T cells from said sample;
 iii) In vitro expansion of regulatory T cells
 iv) Modifying genetically said isolated regulatory T cells in order to silence or inactivate the lymphotoxin alpha gene.

As used herein, the term "subject" denotes a mammal, such as a rodent, a feline, a canine, and a primate. Preferably, a subject according to the invention is a human.

As used herein, the term "biological sample" refers to any body fluid or tissue. In one embodiment, the biological sample is blood sample.

As used herein, the term "regulatory T cell immunosuppressive activity" is well-known in the art and refers to the ability of Treg to suppress or downregulate induction and proliferation of effector T cells. As used herein the term "stimulating regulatory T cells immunosuppressive activity" refers to an increase of regulatory T cell immunosuppressive activity. As used herein, "isolating" refers to removal of a cell or a cell population from its natural environment. As used herein, "isolated" refers to a cell or a cell population that is removed from its natural environment (such as the blood sample) and that is isolated, purified or separated, and is at least about 75% free, 80% free, 85% free and preferably about 90%, 95%, 96%, 97%, 98%, 99% free, from other cells with which it is naturally present.

As used herein, the term "modifying genetically" refers to the addition, suppression or substitution of at least one nucleic acid in the genetic material of the cell.

As used herein the term "to silence the lymphotoxin alpha gene" refers to the total or partial suppression of the lymphotoxin alpha gene function. This term means that the gene coding for lymphotoxin alpha is deleted from the genome or mutated resulting on a non-viable RNA. According to the method of the present invention, the regulatory T cells of the invention are isolated from the sample. All the techniques known by the skilled man may be used.

In one embodiment, the regulatory T cells are isolated by cell sorter after pre-enrichment of CD4$^+$ T cells by depletion of CD8$^+$ and CD19$^+$ cells. The purity of sorted regulatory T cells was >97%.

According to the present invention, the regulatory T cell of the invention is genetically modified in order to silence the lymphotoxin alpha gene. In particular, the gene coding for lymphotoxin alpha is deleted or mutated resulting on a non-viable RNA.

All the techniques known by the skilled man may be used for silencing the lymphotoxin alpha gene.

In one embodiment, ribozyme, antisense oligonucleotides, siRNAs or shRNAs are used for silencing the lymphotoxin alpha gene.

Ribozymes can function as inhibitors of lymphotoxin alpha gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of lymphotoxin alpha mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Anti-sense oligonucleotides include anti-sense RNA molecules and anti-sense DNA molecules, that would act to directly block the translation of the targeted mRNA by binding thereto and thus preventing protein translation or increasing mRNA degradation, thus decreasing the level of the targeted protein, and thus activity, in a cell. For example, antisense oligonucleotides of at least about 15 bases and complementary to unique regions of the mRNA transcript sequence can be synthesized, e.g., by conventional phosphodiester techniques. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can function as inhibitors of gene expression for use in the present invention. Lymphotoxin alpha gene expression can be reduced by contacting a subject or cell with a small double stranded RNA (dsRNA), or a vector or construct causing the production of a small double stranded RNA, such that lymphotoxin alpha gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

A short hairpin RNA (shRNA) is a sequence of RNA that makes a tight hairpin turn that can be used to silence gene expression via RNA interference. shRNA is generally expressed using a vector introduced into cells, wherein the vector utilizes the U6 promoter to ensure that the shRNA is always expressed. The shRNA hairpin structure is cleaved by the cellular machinery into siRNA, which is then bound to the RNA-induced silencing complex (RISC). This complex binds to and cleaves mRNAs that match the siRNA to which it is bound. Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway whereby the siRNA interferes with the expression of a specific gene.

Both antisense oligonucleotides and ribozymes useful as inhibitors of lymphotoxin alpha gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides, siRNAs, shRNAs of the invention may be delivered in vivo alone or in association with a vector. In its broadest sense, a "vector" is any vehicle capable of facilitating the transfer of the antisense oligonucleotide, siRNA, shRNA or ribozyme nucleic acid to the cells and typically mast cells. Classically, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line—with plasmid, production of recombinant retroviruses by the packaging cell line, collection of viral particles from tissue culture media, and infection of the target cells with viral particles) are provided in Kriegler, 1990 and in Murry, 1991. Preferred viruses for certain applications are the adeno-viruses and adeno-associated viruses, which are double-stranded DNA viruses. The adeno-associated virus can be engineered to be replication deficient and is capable of infecting a wide range of cell types and species. It further has advantages such as, heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion. Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter.

In one embodiment, an endonuclease is used for silencing the lymphotoxin alpha gene. In one embodiment, the "CRISPR/Cas9" technology is used for silencing the lymphotoxin alpha gene. As used herein, the term "CRISPR" has its general meaning in the art and refers to clustered regularly interspaced short palindromic repeats associated which are the segments of prokaryotic DNA containing short repetitions of base sequences. In bacteria the CRISPR/Cas loci encode RNA-guided adaptive immune systems against mobile genetic elements (viruses, transposable elements and conjugative plasmids). Three types (I-III) of CRISPR systems have been identified. CRISPR clusters contain spacers, the sequences complementary to antecedent mobile elements. CRISPR clusters are transcribed and processed into mature CRISPR (Clustered Regularly Interspaced Short Palindromic Repeats) RNA (crRNA). The CRISPR-associated endonuclease, Cas9, belongs to the type II CRISPR/Cas system and has strong endonuclease activity to cut target DNA. Cas9 is guided by a mature crRNA that contains about base pairs (bp) of unique target sequence (called spacer) and a trans-activated small RNA (tracrRNA) that serves as a guide for ribonuclease Ill-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM). The crRNA and tracrRNA can be expressed separately or engineered into an artificial fusion small guide RNA (sgRNA) via a synthetic stem loop to mimic the natural crRNA/tracrRNA duplex. Such sgRNA, like shRNA, can be synthesized or in vitro transcribed for direct RNA transfection or expressed from U6 or HI-promoted RNA expression vector, although cleavage efficiencies of the artificial sgRNA are lower than those for systems with the crRNA and tracrRNA expressed separately. In some embodiments, the CRISPR-associated endonuclease can be a Cas9 nuclease. The Cas9 nuclease can have a nucleotide sequence identical to the wild type *Streptococcus* pyrogenes sequence. In some embodiments, the CRISPR-associated endonuclease can be a sequence from other species, for example other *Streptococcus* species, such as *thermophilus; Pseudomonas aeruginosa, Escherichia coli*, or other sequenced bacteria genomes and archaea, or other prokaryotic microoganisms. Alternatively, the wild type *Streptococcus* pyrogenes Cas9 sequence can be modified. The nucleic acid sequence can be codon optimized for efficient expression in mammalian cells, i.e., "humanized." A humanized Cas9 nuclease sequence can be for example, the Cas9 nuclease sequence encoded by any of the expression vectors listed in Genbank accession numbers KM099231.1 GL669193757; KM099232.1 GL669193761; or KM099233.1 GL669193765. Alternatively, the Cas9 nuclease sequence can be for example, the sequence contained within a commercially available vector such as PX330 or PX260 from Addgene (Cambridge, MA). In some embodiments, the Cas9 endonuclease can have an amino acid sequence that is a variant or a fragment of any of the Cas9 endonuclease sequences of Genbank accession numbers KM099231.1 GL669193757; KM099232.1; GL669193761; or KM099233.1 GL669193765 or Cas9 amino acid sequence of PX330 or PX260 (Addgene, Cambridge, MA). The Cas9 nucleotide sequence can be modified to encode biologically active variants of Cas9, and these variants can have or can include, for example, an amino acid sequence that differs from a wild type Cas9 by virtue of containing one or more mutations (e.g., an addition, deletion, or substitution mutation or a combination of such mutations). One or more of the substitution mutations can be a substitution (e.g., a conservative amino acid substitution). For example, a biologically active variant of a Cas9 polypeptide can have an amino acid sequence with at least or about 50% sequence identity (e.g., at least or about 50%, 55%, 60%, 65%, 70%, 75%, 80%, 85%, 90%, 95%), 97%), 98%), or 99% sequence identity) to a wild type Cas9 polypeptide. Conservative amino acid substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. The Cas9 nuclease sequence can be a mutated sequence. For example the Cas9 nuclease can be mutated in the conserved FiNH and RuvC domains, which are involved in strand specific cleavage. For example, an aspartate-to-alanine (D10A) mutation in the RuvC catalytic domain allows the Cas9 nickase mutant (Cas9n) to nick rather than cleave DNA to yield single-stranded breaks, and the subsequent preferential repair through HDR can potentially decrease the frequency of unwanted indel mutations from off-target double-stranded breaks. The polypeptides that are biologically active variants of a CRISPR-associated endonuclease can be characterized in terms of the extent to which their sequence is similar to or identical to the corresponding wild-type polypeptide. For example, the sequence of a biologically active variant can be at least or about 80% identical to corresponding residues in the wild-type polypeptide. For example, a biologically active variant of a CRISPR-associated endonuclease can have an amino acid sequence with at least or about 80% sequence identity (e.g., at least or about 85%, 90%, 95%, 97%, 98%, or 99% sequence identity) to a CRISPR-associated endonuclease or to a homolog or ortholog thereof. A biologically active variant of a CRISPR-associated endonuclease polypeptide will retain sufficient biological activity to be useful in the present methods. The biologically active variants will retain sufficient activity to function in targeted DNA cleavage. The biological activity can be assessed in ways known to one of ordinary skill in the art and includes, without limitation, in vitro cleavage assays or functional assays.

It has already been successfully used to target important genes in many cell lines and organisms, including human (Mali et al., 2013, Science, Vol. 339: 823-826), bacteria (Fabre et al., 2014, PLoS Negl. Trop. Dis., Vol. 8:e2671), zebrafish (Hwang et al., 2013, PLoS One, Vol. 8:e68708), *C. elegans* (Hai et al., 2014 Cell Res. doi: 10.1038/cr.2014.11), bacteria (Fabre et al., 2014, PLoS Negl. Trop. Dis., Vol. 8:e2671), plants (Mali et al., 2013, Science, Vol. 339: 823-826), *Xenopus tropicalis* (Guo et al., 2014, Development, Vol. 141: 707-714), yeast (DiCarlo et al., 2013, Nucleic Acids Res., Vol. 41: 4336-4343), *Drosophila* (Gratz et al., 2014 Genetics, doi:10.1534/genetics.113.160713), monkeys (Niu et al., 2014, Cell, Vol. 156: 836-843), rabbits (Yang et al., 2014, J. Mol. Cell Biol., Vol. 6: 97-99), pigs (Hai et al., 2014, Cell Res. doi: 10.1038/cr.2014.11), rats (Ma et al., 2014, Cell Res., Vol. 24: 122-125) and mice (Mashiko et al., 2014, Dev. Growth Differ. Vol. 56: 122-129).

In some embodiment, the endonuclease is CRISPR-Cpf1 which is the more recently characterized CRISPR from Provotella and *Francisella* 1 (Cpf1) in Zetsche et al. ("Cpf1 is a Single RNA-guided Endonuclease of a Class 2 CRISPR-Cas System (2015); Cell; 163, 1-13).

Regulatory T Cells of the Invention Expressing Chimeric Antigen Receptor

A further object of the present invention relates to the regulatory T cell of the invention characterized in that it expresses a chimeric antigen receptor which recognizes/binds to an autoantigen.

The term "Chimeric Antigen Receptor" or "CAR" has its general meaning in the art and refers to an artificially constructed hybrid protein or polypeptide containing the antigen binding domains of an antibody (e.g., scFv) linked to T-cell signaling domains. In the context of the invention, the antigen binding domains of the antibody recognizes/binds to an autoantigen.

As used herein, the term "recognizes" or "binds" means in the context of the invention that the chimeric antigen receptor has affinity for an antigen.

As used herein, the term "autoantigen" refers to an endogenous antigen, or an active fragment thereof, that is recognized by the immune system.

Auto-antigens comprise, but are not limited to, cellular proteins, phosphoproteins, cellular surface proteins, cellular lipids, nucleic acids, glycoproteins, including cell surface receptors. Examples of auto-antigens include but are not limited to preproinsulin (PPI), glutamic acid decarboxylase (GAD), insulinoma-associated protein 2 (IA-2), islet-specific glucose-6-phosphatase catalytic-subunit-related protein (IGRP), zinc transporter 8 (ZnT8) and chromogranin A for T1D; myeloperoxydase and proteinase 3 for granulomatosis with polyangiitis; myelin oligodendrocyte glycoprotein (MOG) and myelin basic protein (MBP) in multiple sclerosis; and gliadins in celiac disease.

Another object relates to a population of regulatory T cells of the invention characterized in that it expresses a chimeric antigen receptor which recognizes/binds to an autoantigen.

Another object of the present invention relates to a method of producing the regulatory T cell of the invention expressing a chimeric antigen receptor which recognizes/binds to an autoantigen, which comprises the step of transfecting or transducing a regulatory T cell of the invention in vitro or ex vivo with a vector encoding for the chimeric antigen receptor.

The term "transduction" or "transducing" refers to the viral transfer of genetic material and its expression in a recipient cell.

The term "transfection" or "transfecting" as used herein refers to the process of introducing DNA (e.g., formulated DNA expression vector) into a cell, thereby, allowing cellular transformation.

As used herein, the term "vector" refers to a nucleic acid molecule allowing insertion of foreign nucleic acid without disrupting the ability of the vector to replicate and/or integrate in a host cell.

Methods of Treatment

The regulatory T cells populations of the present invention (population of regulatory T cells characterized in that it does not express or expresses reduced levels of lymphotoxin alpha and population of regulatory T cells characterized in that it does not express or expresses reduced levels of lymphotoxin alpha and in that it expresses a chimeric antigen receptor which recognizes/binds to an autoantigen) are particularly suitable for therapeutic uses.

Accordingly, a further object of the present invention relates to the population of regulatory T cells characterized in that it does not express or expresses reduced levels of lymphotoxin alpha and/or the population of regulatory T cells characterized in that it does not express or expresses reduced levels of lymphotoxin alpha and in that it expresses a chimeric antigen receptor which recognizes/binds to an autoantigen for use in adoptive cell therapy in a subject in need thereof. The term "adoptive cell therapy" as used herein refers to a cell-based immunotherapy that relates to the transfusion of autologous or allogenic lymphocytes, genetically modified or not. For the purpose of the present invention, the regulatory T cells are genetically modified. The populations of Treg of the present invention can be utilized in methods and compositions for adoptive cell therapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the age and weight of the recipient, on the severity of the targeted condition. Classically, the number of Treg to be injected is about $1-3\times10^6$/kg (Adair et al. Human Tregs Made Antigen Specific by Gene Modification: The Power to Treat Autoimmunity and Antidrug Antibodies with Precision. Front Immunol 2017). However, the dosage may be reduced when using the Treg of the invention because their immunosuppressive activity is increased. In one embodiment, the dosage may be reduced at least by 50%. In one embodiment, the dosage may be reduced by 75%. In one embodiment, the standard cell therapy dosages may be used: these amount of cells may be as low as approximately $10^3$/kg, preferably $5\times10^3$/kg; and as high as $10^7$/kg, preferably $10^8$/kg. The number of cells will depend upon the ultimate use for which the composition is intended, as will the type of cells included therein. The clinically relevant number of immune cells can be apportioned into multiple infusions that cumulatively equal or exceed the desired total amount of cells.

For the purpose of the invention, the regulatory T cells used in the adoptive cell therapy may be isolated from the subject ("autologous cells") or from another individual ("allogeneic cells").

As used herein, "allogeneic cells" refers to cells isolated from one subject (the donor) an infused in another (the recipient or host).

As used herein, "autologous cells" refers to cells that are isolated and infused back into the same subject (recipient or host).

In one embodiment, the regulatory T cells used in the adoptive cell therapy may derived from stem cells.

The terms "stem cell" as used herein, refer to a cell in an undifferentiated or partially differentiated state that has the property of self-renewal and has the developmental potential to differentiate into multiple cell types, without a specific implied meaning regarding developmental potential (i.e., totipotent, pluripotent, multipotent, etc.).

In a particular embodiment, the regulatory T cells used in the adoptive cell therapy may derived from induced pluripotent stem cells.

As used herein, the terms "iPSC" and "induced pluripotent stem cell" are used interchangeably and refers to a pluripotent stem cell artificially derived (e.g., induced or by complete reversal) from a non-pluripotent cell, typically an adult somatic cell, for example, by inducing a forced expression of one or more genes.

In a particular embodiment, the regulatory T cells used in the adoptive cell therapy may derived from embryonic stem cells.

The term "embryonic stem cell" as used herein refers to naturally occurring pluripotent stem cells of the inner cell mass of the embryonic blastocyst (see, for e.g., U.S. Pat. Nos. 5,843,780; 6,200,806; 7,029,913; 7,584,479, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). Embryonic stem cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta, i.e., are not totipotent. In one embodiment, the regulatory T cells used in the adoptive cell therapy may derived from the conversion of conventional CD4+ T cells.

A further object of the present invention relates to a method of treating autoimmune disease in a subject in need thereof, said method comprising administering to the subject a therapeutically effective amount of the population of regulatory T cells characterized in that it does not express or expresses reduced levels of lymphotoxin alpha and/or the population of regulatory T cells characterized in that it does not express or expresses reduced levels of lymphotoxin alpha and in that it expresses a chimeric antigen receptor which recognizes/binds to an autoantigen.

As used herein, the term "autoimmune disease" refers to the presence of an autoimmune response (an immune response directed against an auto- or self-antigen) in a subject. Autoimmune diseases include diseases caused by a breakdown of self-tolerance such that the adaptive immune system, in concert with cells of the innate immune system, responds to self-antigens and mediates cell and tissue damage. In some embodiments, autoimmune diseases are characterized as being a result of, at least in part, a humoral and/or cellular immune response. Examples of autoimmune disease include, without limitation, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/Anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, autoimmune urticaria, axonal and neuronal neuropathies, Behcet's disease, bullous pemphigoid, autoimmune cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic fasciitis, erythema nodosum, experimental allergic encephalomyelitis, Evans syndrome, fibromyalgia, fibrosing alveolitis, giant cell arteritis (temporal arteritis), glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, hypergammaglobulinemia, idiopathic thrombocytopenic purpura (ITP), IgA nephropathy, IgG4-related sclerosing disease, immunoregulatory lipoproteins, inclusion body myositis, inflammatory bowel disease, insulin-dependent diabetes (type 1), interstitial cystitis, juvenile arthritis, Kawasaki syndrome, Lambert-Eaton syndrome, leukocytoclastic vasculitis, lichen planus, lichen sclerosus, ligneous conjunctivitis, linear IgA disease (LAD), lupus (SLE), Lyme disease, Meniere's disease, microscopic polyangiitis, mixed connective tissue disease (MCTD), monoclonal gammopathy of undetermined significance (MGUS), Mooren's ulcer, Mucha-Habermann disease, multiple sclerosis, myasthenia gravis, myositis, narcolepsy, neuromyelitis optica (Devic's), autoimmune neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomenon, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/Giant cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, Waldenstrom's macroglobulinemia (WM), and Wegener's granulomatosis [Granulomatosis with Polyangiitis (GPA)]. In some embodiments, the autoimmune disease is selected from the group consisting of rheumatoid arthritis, type 1 diabetes, systemic lupus erythematosus (lupus or SLE), myasthenia gravis, multiple sclerosis, scleroderma, Addison's Disease, bullous pemphigoid, pemphigus vulgaris, Guillain-Barré syndrome, Sjogren syndrome, dermatomyositis, thrombotic thrombocytopenic purpura, hypergammaglobulinemia, monoclonal gammopathy of undetermined significance (MGUS), Waldenstrom's macroglobulinemia (WM), chronic inflammatory demyelinating polyradiculoneuropathy (CIDP), Hashimoto's Encephalopathy (HE), Hashimoto's Thyroiditis, Graves' Disease, Wegener's Granulomatosis [Granulomatosis with Polyangiitis (GPA)].

In one embodiment, the autoimmune disease is inflammatory bowel disease.

In one embodiment, the autoimmune disease is multiple sclerosis or type 1 diabetes.

A further object of the present invention relates to a method of treating inflammation-associated cancer in a subject in need thereof, said method comprising administering to the subject a therapeutically effective amount of the population of regulatory T cells characterized in that it does not express or expresses reduced levels of lymphotoxin alpha.

As used herein, the term "inflammation-associated cancer" refers to any cancer for which inflammation is considered to be at least one of the pathogenesis mechanisms involved in the cancer initiation and development. Examples of inflammation-associated cancer include, but it is not limited to, colitis-associated cancer, gastric adenocarcinoma, bladder carcinoma, liver carcinoma, rectal carcinoma, cholangiocarcinoma, colon carcinoma, colorectal carcinoma, Gall bladder cancer, hepatocellular carcinoma, ovarian carcinoma, cervical carcinoma, skin carcinoma, esophageal carcinoma, bladder cancer, mesothelioma, lung cancer, oral squamous cell carcinoma, pancreatic carcinoma, vulvar squamous cell carcinoma, salivary gland carcinoma, lung carcinoma, MALT lymphoma.

In one embodiment, the inflammation-associated cancer is colitis-associated cancer. The colitis-associated cancer is a subtype of colorectal cancer.

A further object of the present invention relates to a method of treating allergy in a subject in need thereof, said method comprising administering to the subject a therapeutically effective amount of the population of regulatory T cells characterized in that it does not express or expresses reduced levels of lymphotoxin alpha.

As used herein, the term "allergy" generally refers to an inappropriate immune response characterized by inflammation and includes, without limitation, food allergies, respiratory allergies and other allergies causing or with the potential to cause a systemic response such as, by way of example, Quincke's oedema and anaphylaxis. The term encompasses allergy, allergic disease, hypersensitive associated disease or respiratory disease associated with airway inflammation, such as asthma or allergic rhinitis. In some embodiments, the method of the present invention is effective in preventing, treating or alleviating one or more symptoms related to anaphylaxis, drug hypersensitivity, skin allergy, eczema, allergic rhinitis, urticaria, atopic dermatitis, dry eye disease, allergic contact allergy, food hypersensitivity, allergic conjunctivitis, insect venom allergy, bronchial asthma, allergic asthma, intrinsic asthma, occupational asthma, atopic asthma, acute respiratory distress syndrome (ARDS) and chronic obstructive pulmonary disease (COPD). Hypersensitivity associated diseases or disorders that may be treated by the method of the present invention include, but are not limited to, anaphylaxis, drug reactions, skin allergy, eczema, allergic rhinitis, urticaria, atopic dermatitis, dry eye disease [or otherwise referred to as Keratoconjunctivitis sicca (KCS), also called keratitis sicca, xerophthalmia], allergic contact allergy, food allergy, allergic conjunctivitis, insect venom allergy and respiratory diseases associated with airway inflammation, for example, IgE mediated asthma and non-IgE mediated asthma. The respiratory diseases associated with airway inflammation may include, but are not limited to, rhinitis, allergic rhinitis, bronchial asthma, allergic (extrinsic) asthma, non-allergic (intrinsic) asthma, occupational asthma, atopic asthma, exercise induced asthma, cough-induced asthma, acute respiratory distress syndrome (ARDS) and chronic obstructive pulmonary disease (COPD). A further object of the present invention relates to a method of treating immune reactions against molecules that are exogenously administered in a subject in need thereof, said method comprising administering to the subject a therapeutically effective amount of the population of regulatory T cells characterized in that it does not express or expresses reduced levels of lymphotoxin alpha.

Non-limiting examples of this kind include immune reactions against replacement therapeutics in the context of genetic deficiencies, which include, but are not limited to, haemophilia A, haemophilia B, congenital deficiency of other clotting factors such as factor II, prothrombin and fibrinogen, primary immunodeficiencies (e.g. severe combined immunodeficiency, X-linked agammaglobulinemia, IgA deficiency), primary hormone deficiencies such as growth hormone deficiency and leptin deficiency, congenital enzymopathies and metabolic disorders such as disorders of carbohydrate metabolism (e.g. sucrose-isomaltase deficiency, glycogen storage diseases), disorders of amino acid metabolism (e.g. phenylketonuria, maple syrup urine disease, glutaric acidemia type 1), urea cycle disorders (e.g. carbamoyl phosphate synthetase I deficiency), disorders of organic acid metabolism (e.g. alcaptonuria, 2-hydroxyglutaric acidurias), disorders of fatty acid oxidation and mitochondrial metabolism (e.g. medium-chain acyl-coenzyme A dehydrogenase deficiency), disorders of porphyrin metabolism (e.g. porphyrias), disorders of purine or pyrimidine metabolism (e.g. Lesch-Nyhan syndrome), disorders of steroid metabolism (e.g. lipoid congenital adrenal hyperplasia, congenital adrenal hyperplasia), disorders of mitochondrial function (e.g. Kearns-Sayre syndrome), disorders of peroxisomal function (e.g. Zellweger syndrome), lysosomal storage disorders (e.g. Gaucher's disease, Niemann Pick disease).

A further object of the present invention relates to a method of treating immune reactions against a grafted tissue or grafted cells in a subject in need thereof, said method comprising administering to the subject a therapeutically effective amount of the population of regulatory T cells characterized in that it does not express or expresses reduced levels of lymphotoxin alpha.

As used herein, the term "grafted" refers to organs and/or tissues and/or cells which can be obtained from a first organism (or donor) and transplanted into a second organism (or recipient. Typically the subject may have been transplanted with a graft selected from the group consisting of heart, kidney, lung, liver, pancreas, pancreatic islets, brain tissue, stomach, large intestine, small intestine, cornea, skin, trachea, bone, bone marrow, muscle, or bladder. The method of the present invention is also particularly suitable for preventing or suppressing an immune response associated with rejection of a donor tissue, cell, graft, or organ transplant by a recipient subject. Graft-related diseases or disorders include graft versus host disease (GVHD), such as associated with bone marrow transplantation, and immune disorders resulting from or associated with rejection of organ, tissue, or cell graft transplantation (e.g., tissue or cell allografts or xenografts), including e.g., grafts of skin, muscle, neurons, islets, organs, parenchymal cells of the liver, etc. Thus the method of the invention is useful for preventing Host-Versus-Graft-Disease (HVGD) and Graft-Versus-Host-Disease (GVHD). The chimeric construct may be administered to the subject before, during and/or after transplantation (e.g., at least one day before transplantation, at least one day after transplantation, and/or during the transplantation procedure itself). In some embodiments, the chimeric construct may be administered to the subject on a periodic basis before and/or after transplantation.

As used herein, the term "subject" denotes a mammal, such as a rodent, a feline, a canine, and a primate. Preferably, a subject according to the invention is a human.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. The term "treatment" encompasses the prophylactic treatment. As used herein, the term "prevent" refers to the reduction in the risk of acquiring or developing a given condition.

As used herein the terms "administering" or "administration" refer to the act of injecting or otherwise physically delivering a substance as it exists outside the body into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

The "therapeutically effective amount" is determined using procedures routinely employed by those of skill in the art such that an "improved therapeutic outcome" results. It will be understood, however, that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination; and like factors well known in the medical arts. According to the invention, the populations of regulatory T cells are administered to the subject in the form of a pharmaceutical composition.

Accordingly, a further object of the present invention relates to a pharmaceutical composition comprising the population of regulatory T cells characterized in that it does not express or expresses reduced levels of lymphotoxin alpha and/or the population of regulatory T cells characterized in that it does not express expresses reduced levels of lymphotoxin alpha and in that in that it expresses a chimeric antigen receptor which recognizes/binds to an autoantigen. Typically, the populations of Tregs may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. In one embodiment, the Treg populations of the invention are administered by parenteral route. In a preferred embodiment, the Treg populations of the invention are administered by intravenous route. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The populations of Tregs can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIG. 1A-D. Thymic Foxp3+ Tregs from LTα−/− mice show a highly suppressive signature. (A) The expression of Ltα and Ltβ was measured by qPCR in purified Foxp3-GFP-conventional CD4+SP thymocytes and Foxp3-GFP+ CD4+CD8− Tregs from adult Foxp3-GFP reporter mice (n=3 experiments). (B) Representative histogram showing the expression of the cell surface LTα1β2 heterotrimer (detected by staining with the soluble LTβR-Fc protein) in conventional Foxp3− CD4+SP and Foxp3+CD4+ Treg cells from WT thymi (n=6). Data are pooled of 2 independent experiments (n=3-4 mice per group). (C) Representative histograms showing the expression of the cell surface LTα1β2 heterotrimer (detected by staining with the soluble LTβR-Fc protein) in Foxp3$^+$ nTregs (n=20), Foxp3$^+$ nTregs stimulated 0/N with anti-CD3/CD28 antibodies (n=5), Foxp3$^+$ iTregs (n=6) and CD8$^+$CD28$^{lo}$ Tregs (n=6) derived from the spleen of WT mice. (D) The expression level of Il10, Ebi3, Tgfb1, Ifng, Gzmb and Fas1 mRNAs was measured by qPCR in CD4+CD25+ thymic Tregs purified from WT (n=3-6) and LTα−/− (n=3-6) adult and postnatal d10 mice. Data are derived from 2 independent experiments (n=3-4 mice per group).

Figure 2:
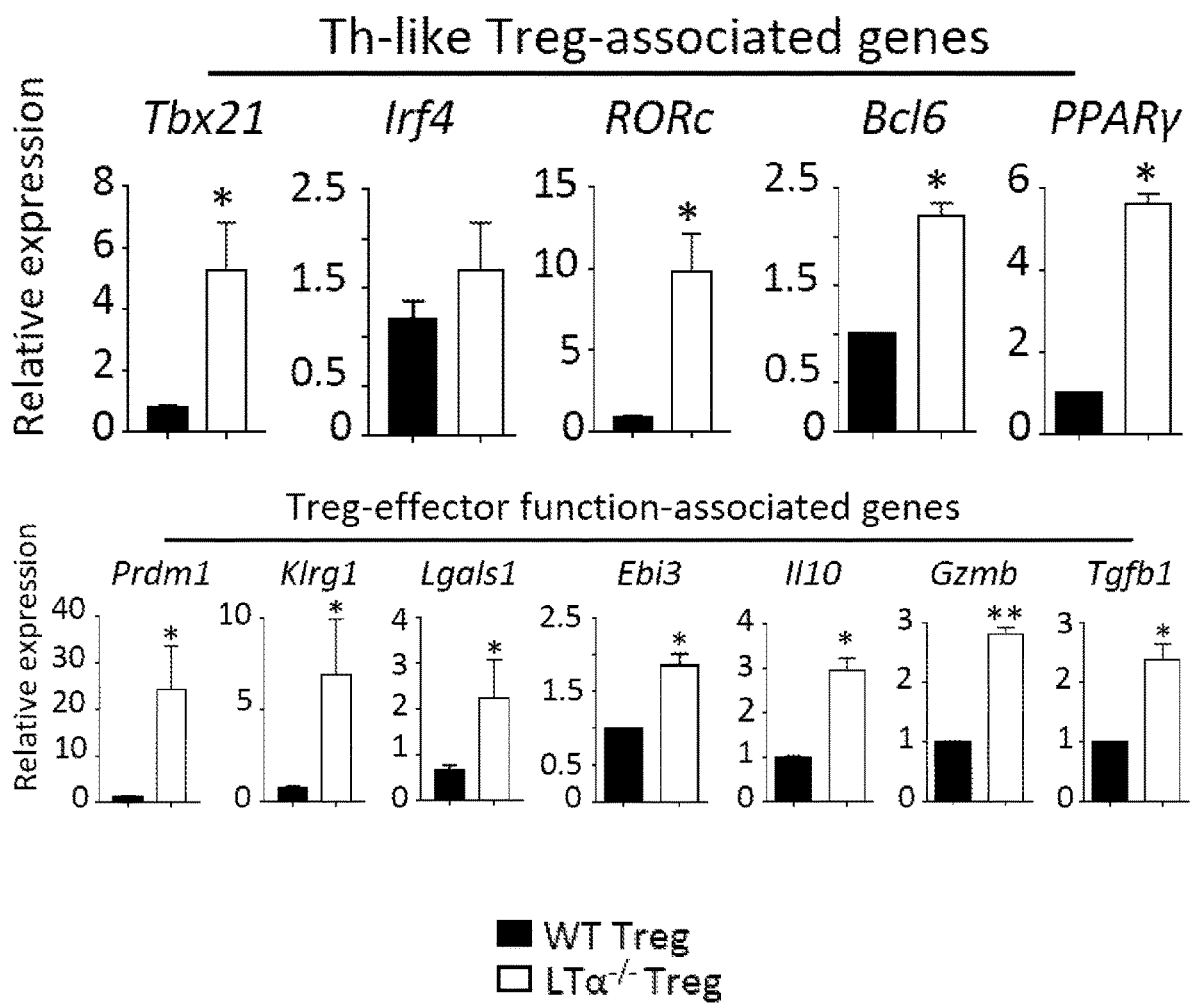

FIG. 2. Peripheral LTα−/− Tregs exhibit an effector phenotype. The expression level of several genes known to be associated with the polarization and effector functions of Tregs was measured by qPCR in purified WT and LTα−/− splenic Tregs (n=3 mice per group).

FIG. 3A-J. The adoptive transfer of LTα−/− Tregs protects from the severity of DSS-induced colitis. (A) Representative flow cytometry profiles of Foxp3 expression in purified splenic CD4+CD25+ cells from WT and LTα−/− mice. (B) Experimental setup: colitis was induced by the administration of 2% DSS in drinking water for 7 days followed by water only until day 11 in WT mice injected 2 days before with $2 \times 10^5$ WT or LTα−/− Tregs. Colon inflammation and CD4+ T cell priming in mesenteric lymph nodes were analyzed at day 11 and day 4 of the protocol, respectively. (C) Body weight loss relative to the initial weight on day 0 of WT mice injected with $2 \times 10^5$ WT or LTα−/− Tregs. Data are derived from 3 independent experiment with 4 mice per group. (D) Disease activity index (DAI) was monitored during the course of DSS-induced colitis. (E) The histogram shows the histological score of the colon in both groups of mice. (F) The expression level of pro-inflammatory cytokines (Il6, Ifng, Tnfa, Il17a, Il1a and Il33) and chemokines (Ccl2 and Cxcl12) was measured by qPCR in colon tissues from mice injected with WT (n=4) or LTα−/− (n=4) Tregs at the end of the protocol. (G) Numbers of Ly6G+ neutrophils, F4/80+CD11b+ macrophages, CD11b+CD11c+ and CD8α+CD11c+ dendritic cells (DCs), CD19+ B cells and CD4+ T cells observed in the colon of both groups. Data are derived from 2 independent experiments with 4 mice per group. (H) Flow cytometry profiles and numbers of Th1 (CD4+IFN-γ+) and Th17 (CD4+IL-17A+) colon-infiltrating T cells. Data are derived from 3 independent experiment with 4 mice per group. (I) Ratios of Treg/Th1 and Treg/Th17. (J) Body weight loss relative to the initial weight on day 0 of WT mice injected with $2 \cdot 10^5$ WT or $1 \cdot 10^5$ or $0.5 \cdot 10^5$ LTα−/− Tregs. Data are derived from 2 to 3 independent experiments with 4 mice per group.

FIG. 4A-G. The adoptive transfer of LTα−/− Tregs treats from IBD. (A) Experimental setup: Rag2−/− recipient mice were adoptively transferred with CD4+CD25+ Treg-depleted CD45.1 WT splenocytes. Three weeks later when mice developed signs of IBD, they were injected with either $2 \times 10^5$ WT or LTα−/− CD45.2 Tregs. Body weight was monitored during three weeks. (B) Body weight loss relative to the initial weight on day 0 of mice injected with WT or LTα−/− Tregs or untreated. (C) Histograms show colon length and the ratio of colon weight/length observed at the end of the protocol. (D) Flow cytometry profiles and numbers of total colon-infiltrating Foxp3+CD4+ Tregs. (E) Flow cytometry profiles and numbers of colon-infiltrating Foxp3+CD4+ Tregs of CD45.2 origin. (F) Representative flow cytometry profiles and numbers of Th1 (CD4+IFN-γ+) and Th17 (CD4+IL-17A+) colon-infiltrating cells of CD45.1 origin. (G) Ratios of Treg/Th1 and Treg/Th17 in colons.

FIG. 5A-H. The adoptive transfer of LTα−/− Tregs during colon chronic inflammation prevents the development of CAC in the AOM-DSS model. (A) Experimental setup: CD45.1 WT mice were injected with AOM, which initiates tumorigenesis, followed by three cycles of DSS in drinking water, inducing a chronic colitis, which promotes the development of colorectal tumors. $2 \times 10^5$ splenic CD4+CD25+ Tregs purified either from CD45.2 WT or LTα−/− mice were adoptively-transferred in these mice before the first two cycles of DSS. Colons were collected at 3, 6 and 12 weeks after AOM injection. (B-C) Histograms show total numbers of tumors per colon (B) and their volumes (C) at 6 and 12 weeks of the protocol. (D) Histograms show the ratio of colon weight/length at 3, 6 and 12 weeks. (E) The expression level of pro-inflammatory cytokines was measured by qPCR in non tumoral colon tissues from mice injected with WT (n=4) or LTα−/− (n=4) Tregs at 3 and 6 weeks. (F) The histogram shows numbers of total colon infiltrating cells at 3 weeks. (G, H) Frequencies and numbers of Ly6G+ neutrophils, F4/80+CD11b+ and F4/80+CD11b− macrophages, CD11b+CD11c+ and CD11b-CD11c+ DCs, CD4+, CD8+ T cells, Th1, Th17 and CD4+Foxp3+ Tregs in the colon of both groups of mice. Data are derived from 2 independent experiment with 3-4 mice per group.

Figure 6A:
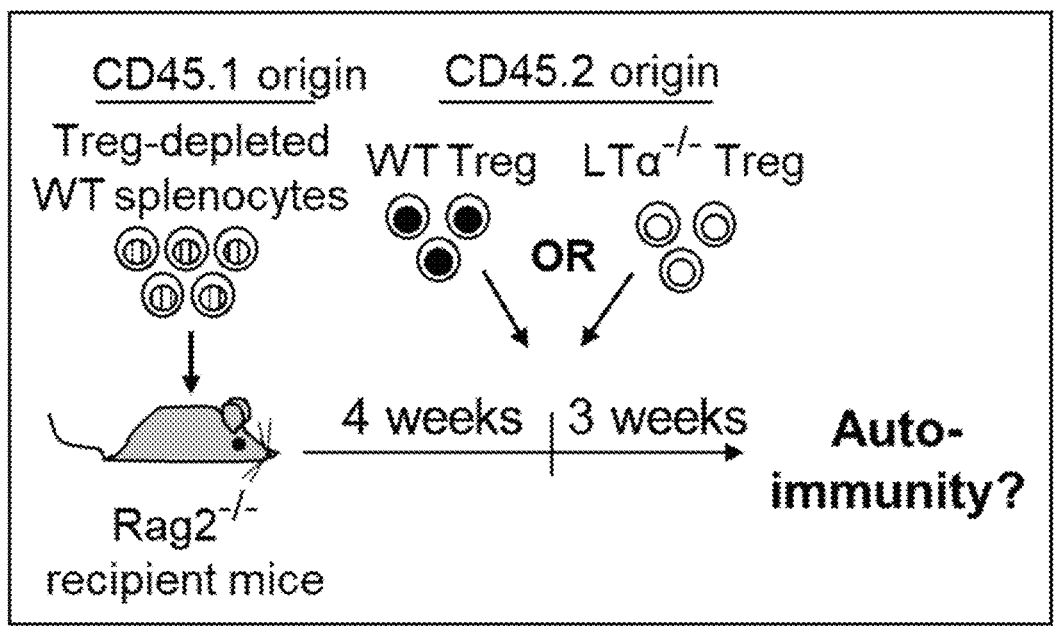
Figure 6B:
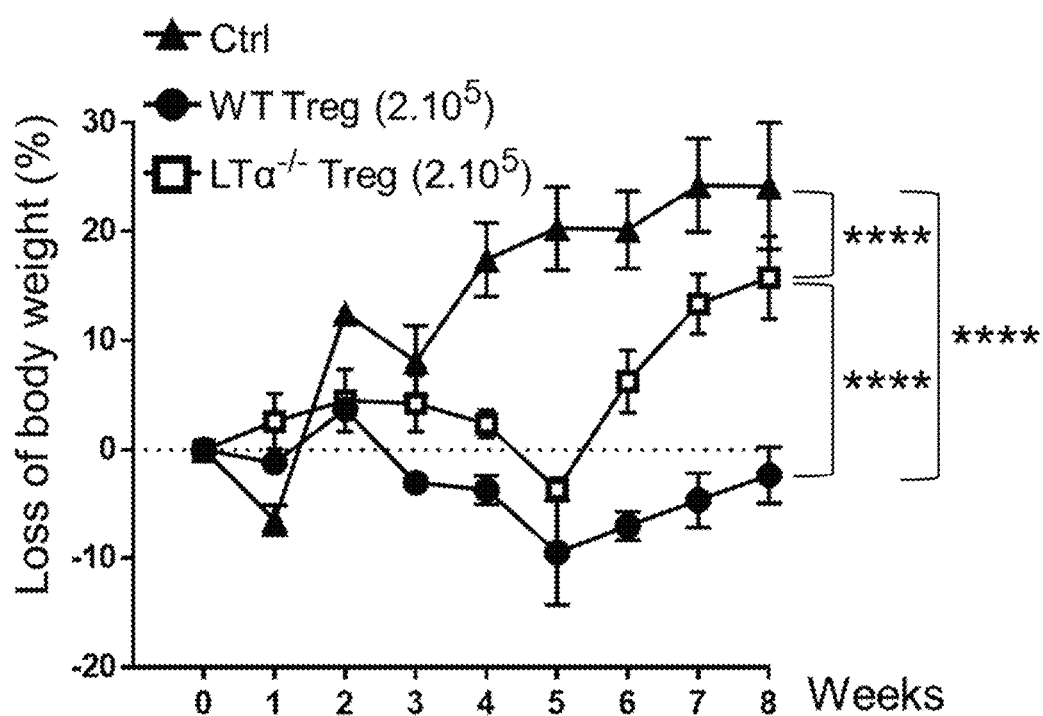
Figure 6C:
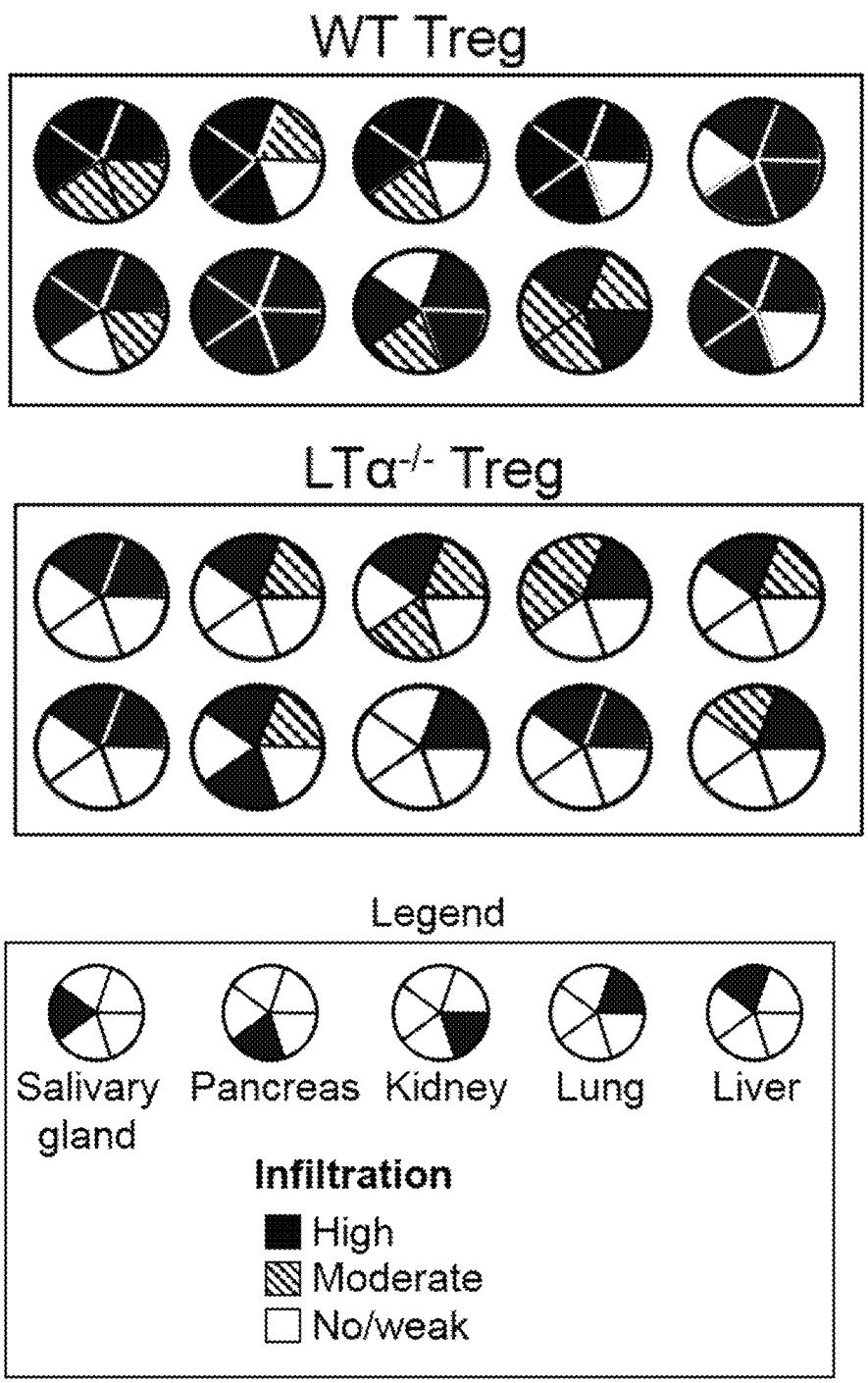

FIG. 6A-C. The adoptive transfer of Ltα$^{-/-}$ Tregs attenuates the severity of multi-organ autoimmunity. (A) Experimental setup: Rag2$^{-/-}$ recipient mice were adoptively transferred with CD4+CD25+ Treg-depleted CD45.1 WT splenocytes. Four weeks later when mice start to loose body weight, they were injected with either $2 \times 10^5$ WT or Ltα$^{-/-}$ CD45.2 Tregs. Three weeks after Treg adoptive transfer, mice were sacrificed and peripheral tissues were examined for immune infiltrates. Rag2$^{-/-}$ recipients co-injected at the beginning of the protocol with CD4+CD25+ Treg-depleted CD45.1 WT splenocytes and CD45.2 WT Tregs were used as controls. (B) Body weight loss relative to the initial weight on day 0 of controls or mice transferred with WT or Ltα$^{-/-}$ Tregs. (C) Diagrams representative of organ infiltration levels by CD45.1 donor cells normalized to the infiltration observed in controls. Each diagram represents one individual mouse.

FIG. 7A-D. The suppressive signature of Treg cells is controlled by the LTα1β2/LTβR axis. (A) Experimental setup: Lethally irradiated WT CD45.1×CD45.2 recipient mice were reconstituted with mixed BM cells from WT CD45.1+WT CD45.2 or WT CD45.1+LTα−/− CD45.2 (ratio 50:50). Six weeks later, CD45.2 WT and CD45.2 LTα−/− from WT and LTα−/− donor groups respectively were cell-sorted and analyzed for several genes associated with Treg suppressive functions. (B) Splenic CD4+ T cells of CD45.2 origin were analyzed by flow cytometry for the expression of Foxp3 in both groups. Histograms show frequencies and numbers of CD45.2 WT and LTα−/− CD4+Foxp3+ Tregs. (C) The expression level of Il10, Ebi3, Tgf-β1, Ifn-γ, Gzmb, Fas1 and Il17a mRNAs was measured by qPCR in purified CD45.2 WT and LTα−/− Tregs from donor groups. (D) Purified WT Foxp3+CD4+ Tregs pre-incubated or not with a soluble LTβR-Fc fusion protein and co-cultured during 24 h with purified CD11c+ DCs were analyzed for the expression level of Klrg1, Il10, Ebi3, Tgfb1, Gzmb, Fas1 and Il17a by qPCR.

Figure 8A:
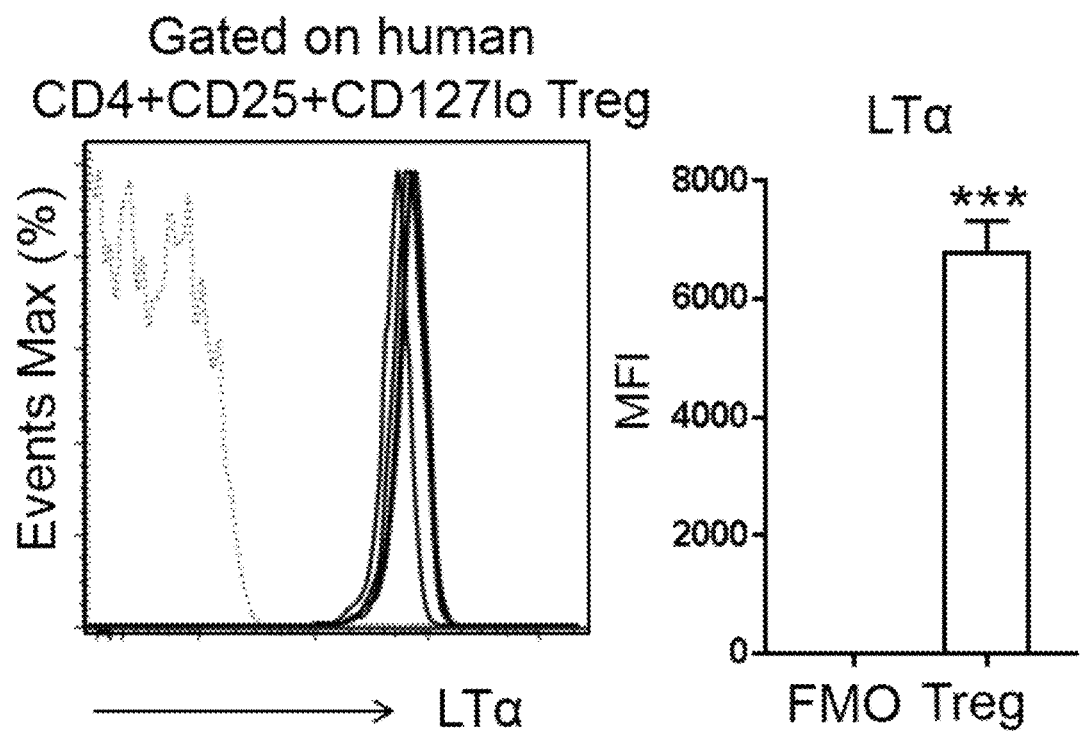
Figure 8B:
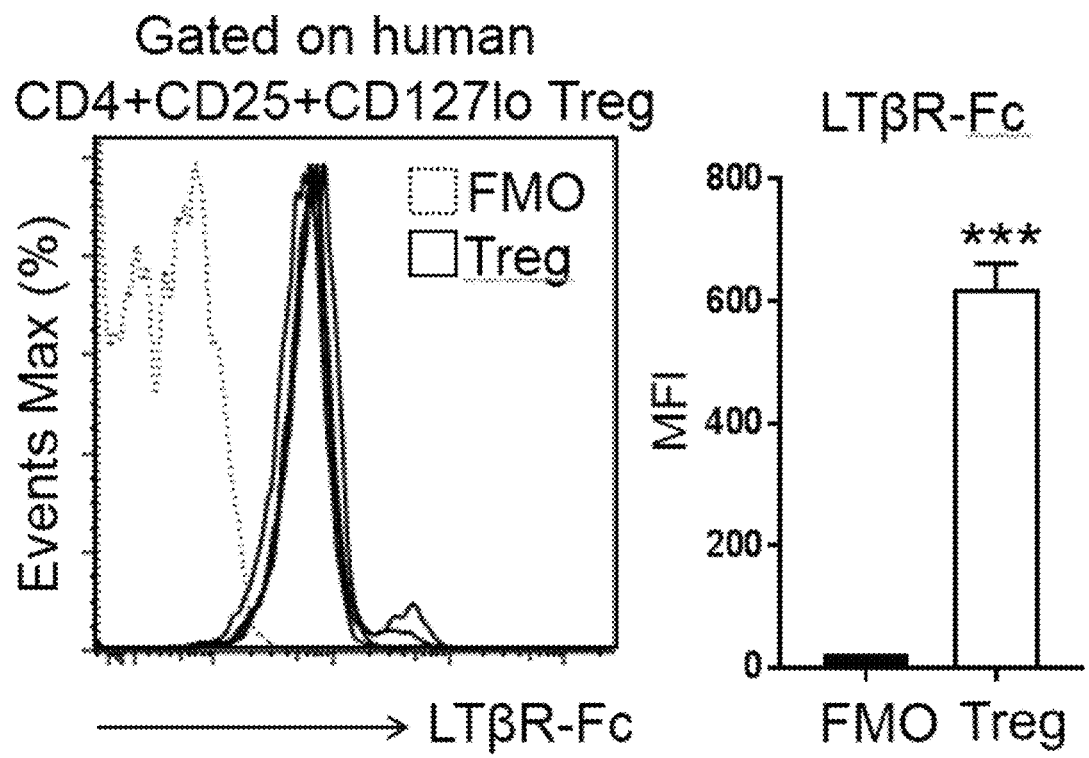

FIG. 8A-B. LTα expression is conserved in human Tregs derived from peripheral blood. Expression of (A) intracellular LTα protein and (B) cell-surface LTα1β2 heterotrimer detected by staining with the soluble LTβR-Fc receptor was analyzed by flow cytometry in CD4$^+$CD25$^-$CD127$^{lo}$ Tregs derived from peripheral blood of male and female patients.

EXAMPLE

Material & Methods
Mice

All mice—CD45.1 WT, CD45.1×CD45.2 WT, CD45.2 WT, CD45.2 LTα−/−, Rag2−/− and Foxp3-GFP reporter mice—were on a pure C57BL/6 background and maintained under specific pathogen free conditions at the CIML (France). Standard food and water were given ad libitum. Males and females were used at d10 after birth or at the age of 6-12 weeks. Chimeras were generated at 6-8 weeks of age. All procedures involving animals have been performed in accordance with the institutional and ethical guidelines.

Healthy Volunteers Blood Collection and PBMCs Separation

Blood was collected at the Etablissement Francais du Sang (Nantes, France) from healthy individuals. Written informed consent was provided according to institutional guidelines. PBMCs were isolated by Ficoll-Paque density-gradient centrifugation (Eurobio, Courtaboeuf, France). Remaining red cells and platelets were eliminated with a hypotonic solution and centrifugation.

BM Chimeras

Before BM transplantation, mice were lethally irradiated with Cs-137 γ-radiation source (2 doses of 500 rads) and transplanted 24h later with 107 BM cells from CD45.1 WT donor with CD45.2 donor (either WT or LTα–/– mice) at ratio 50:50. T-cell reconstitution was assessed by analyzing blood cells by flow cytometry. Mice were analyzed 6 weeks post-reconstitution.

Treg Cell Isolation

Thymic and splenic Treg cells were isolated by scratching thymus and spleen through a 70 μm mesh. Splenic red blood cells were lysed with lysis buffer (eBioscience). Before cell-sorting, CD4+ T cells were pre-enriched by depletion of CD8+ and CD19+ cells using anti-CD8a (clone 53.6.7) and anti-CD19 (clone 1D3) biotinylated antibodies with anti-biotin microbeads by AutoMACS (Miltenyi Biotech) via the deplete program. CD4+CD25+ Tregs were sorted using a FACSAriaIII cell sorter (BD).

LTα–/– Treg Stability In Vivo $2 \cdot 10^5$ CD4+CD25+ splenic Tregs purified from CD45.1 WT and CD45.2 LTα–/– mice were adoptively transferred intravenously into sub-lethally irradiated CD45.1×CD45.2 WT recipient mice (ratio 50:50). Seven days after transfer, CD45.1 WT and CD45.2 LTα–/– CD4+CD25+ splenic Tregs were purified with a FACSAriaIII cell sorter (BD).

RNA-Seq Experiments

CD4+CD25+ splenic Tregs were cell-sorted from WT and LTα$^{-/-}$ mice. Two biological replicates were prepared for each condition. Total RNA was extracted using the RNeasy Micro Kit (Qiagen) and treated with DNase I. RNA-seq libraries were prepared using the TruSeq Stranded mRNA kit (Illumina) and sequenced with the Illumina HiSeq 2000 machine to generate datasets of single-end 50 bp reads. The reads were mapped to the mouse reference genome (mm10) using TopHat2 (version 2.0.12), then counted using Cufflinks or Cuffdiff (version 2.2.1) and the mm10 genome GTF gene annotation file (https://support.illumina.com/sequencing/sequencing_software/igenome.html). In addition to read counting, Cuffdiff performs between-sample normalization and was used to calculate the differential gene expression and its statistical significance in LTα–/– vs WT Tregs. Expression levels generated by Cufflinks, as fragments per kilobase of transcript per million mapped reads (FPKM), were processed by the Matrix2png program to generate heat maps of gene expression levels which were normalized to a mean value of 0 and a variance of 1 across the samples. Identification of biological processes accounting for transcriptomic differences between LTα–/– and WT Tregs was performed with GSEA in calculating the enrichment in expression of every gene set defining a Gene Ontology (GO) biological process (c5.bp.v5.1) and in selecting the processes that are the most enriched. A number of permutations of 10,000 and a "classic" scoring scheme were used to compute the level of enrichment or Normalized Enrichment Score (NES) of a gene set. Null expression values were removed from the analysis. GO biological processes with NES reaching significance (P value<0.05 and FDR<0.25) were selected. Since different GO processes could be defined by gene sets sharing a certain degree of gene overlap, a network representing the GSEA selected processes and their connections depending on their gene set similarities was carried out with Cytoscape. Groups of related GO processes were determined using EnrichmentMap choosing an "Overlap Coefficient" over 0.7. A cluster analysis was performed using ClusterMaker and the implemented "MCL cluster" method. For each cluster of enriched and connected GO biological processes, the process with the most significant enrichment was selected and its NES considered.

DSS-Induced Colitis Experiments

Two days before the induction of colitis, WT recipient mice were injected i.v. with $2 \cdot 10^5$ CD4+CD25+ splenic Tregs sorted from WT or LTα–/– mice or alternatively with $1 \cdot 10^5$ splenic LTα–/– Tregs when mentioned. The induction of colitis was assessed by given 2% DSS (Alfa Aesar) in drinking water for 7 days, followed by only water until sacrifice at d11. Body weight, rectal bleeding and stool consistency were monitored every day after DSS administration and used to determine the DAI.

IBD Experiments

Rag2–/– recipient mice were injected i.v. with $5 \cdot 10^5$ CD4+CD25+ Treg-depleted naive CD4+ T cells purified from CD45.1 WT mice. After 3-4 weeks, $2 \cdot 10^5$ CD4+CD25+ splenic Tregs sorted from CD45.2 WT or LTα–/– mice were injected i.v. Body weight was monitored once per week during the course of IBD.

Colitis-Associated Cancer (CAC) Experiments

WT CD45.1 recipient mice were injected i.p. with Azoxymethane (AOM, 12.5 mg/kg, Sigma). After 5 days, 2.5% DSS (Alfa Aesar) was given in the drinking water over 5 days, followed by 16 days of tap water. This cycle was repeated twice (5 days of 2.5% DSS and 4 days of 2% DSS). $2 \cdot 10^5$ CD4+CD25+ splenic WT Tregs or LTα–/– were injected i.v. in these mice before the first two cycles of DSS. Colons were collected at 3, 6 and 12 weeks after AOM administration.

Multi-Organ Autoimmunity Experiments

Rag2$^{-/-}$ recipient mice were injected i.v. with $3 \cdot 10^6$ CD4+CD25+ Treg-depleted splenocytes purified from CD45.1 WT mice. Four weeks later, $2 \cdot 10^5$ CD4+CD25+ splenic Tregs from CD45.2 WT or Ltα$^{-/-}$ mice were adoptively transferred i.v. Controls concomitantly received $2 \cdot 10^5$ CD4+CD25+ splenic Tregs from CD45.2 WT mice and $3 \cdot 10^6$ CD4+CD25+ Treg-depleted splenocytes from CD45.1 WT mice at the beginning of the protocol. Body weight was monitored once per week during the course of the protocol.

Isolation of Lamina Propria Mononuclear Cells from Colonic Tissue

Colons were cut into 0.5 cm pieces, washed in HBSS with 2% FCS, then incubated twice in HBSS 2 mM EDTA at 37° C. under rotation (15 min then 30 min). Pieces were filtered on 70 μm cell strainer and incubated in culture medium (10% FCS, 1% Penicillin-Streptomycin and 1.5% HEPES in RPMI medium) with 1 mg/ml Collagenase VIII (Sigma) at 37° C. under rotation during 45 min. Cells were filtered and isolated by centrifugation with 40/100% Percoll (Sigma) gradient for 20 min at 2100 rpm at room temperature.

In Vitro Co-Culture Assays, Treg Activation and iTreg Generation

For co-culture assays, 2·10³ cell-sorted total CD11$^{hi}$ DCs, CD11c$^{hi}$PDCA-1$^{lo}$, Sirpα$^{+}$CD11c$^{hi}$ PDCA-1$^{lo}$ or CD11c$^{int}$ PDCA-1$^{hi}$ were co-cultured during 24h at 37° C. with 10$^4$ purified CD4$^+$CD25$^+$ Tregs that were or not pre-incubated during 1h with a soluble LTβR-Fc recombinant protein (2 μg/ml; R&D systems). For Treg activation, 5·10$^4$ cell-sorted CD4±CD25+ Tregs were cultured on plastic bound previously coated with anti-CD3ε antibody (5 μg/ml; clone 2C11) in a culture medium containing soluble anti-CD2.8 (1 μg/ml; clone 37.51) in the presence of IL-2 (200 U/ml, Immunotools) and TGF-β (0.2 ng/ml, eBioscience). iTregs were generated in vitro by culturing purified CD4$^+$CD25$^-$ cells on plastic bound previously coated with anti-CD3ε antibody (5 μg/ml; done 2C11) in a culture medium containing soluble anti-CD28 (1 μg/ml; clone 37.51) in the presence of IL-2 (200 U/ml, Immunotools) and TGF-β (20 ng/ml, eBioscience) for 4 days.

Flow Cytometry

Anti-CD4 (RM4.5), CD8α (53.6.7), CD45.1 (A20), CD45.2 (104), CD44 (IM7), CD25 (PC61), CD11b (M1/70), CD19 (1D3), CD62L (MEL-14) and IFN-γ (XMG1.2) antibodies were from BD. Anti-CD69 (H1.2F3), CCR7 (4B12), Qa-2 (695H1-9-9), IL-10 (JESS-16E3), F4/80 (6F12), CD11c (N418), IL-17A (TC11-18H10.1) and CCR6 (29-2L17) antibodies were from BioLegend. Anti-Ly6G (RB6-8C5), KLRG1 (2F1), Ki-67 (SolA15) and Foxp3 (FJK-16s) were from eBioscience. Anti-Slp1 (713412) was from RnD Systems. For intracellular staining of Foxp3, IL-10, IFN-γ, IL-17A and Ki-67, cells were fixed, permeabilized and stained with the Foxp3 staining kit according to the manufacturer's instructions (eBioscience). For detection of cytokines, cells were stimulated for 3 h at 37° C. with phorbol 12-myristate 13-acetate (PMA; ng/mL; Sigma) and ionomycine (1m/mL; Sigma) in the presence of Brefeldin A (5 μg/mL; BD). For staining with LTβR-Fc, cells were incubated with LTβR-Fc (R&D systems) at 1m/106 cells for 45 min on ice. LTβR-Fc staining was visualized using an Alexa Fluor 488-conjugated donkey anti-human IgG F(ab')2 fragment (Jackson ImmunoResearch). Human anti-CD4 (OKT4), CD25 (BC96), CD127 (A019D5) antibodies were purchased from BioLegend. Stained cells were analyzed with FACSCanto II (BD) and data were analyzed using FlowJo software.

Quantitative RT-PCR

Total RNA was isolated with TRIzol (Invitrogen) and cDNA was synthesized with random oligo dT primers and Superscript II reverse transcriptase (Invitrogen). qPCR was performed with SYBR Premix Ex Taq master mix (Takara) on a ABI 7500 fast real-time PCR system (Applied Biosystem). Results were normalized to actin mRNA.

Immunofluorescence Staining

Immunofluorescence staining on thymic sections was performed as described previously by using Alexa Fluor 488-conjugated anti-Foxp3 (FJK-16s; eBioscience) and anti-K14 (AF64, Covance Research) revealed with Cy3-conjugated anti-rabbit (Invitrogen). Sections were counterstained with 1 μg/ml DAPI and mounted with Mowiol (Calbiochem). Images were acquired with a LSM 780 Leica SPSX confocal microscope and quantified with ImageJ software.

Statistical Analysis

Statistical significance was assessed with GraphPad Prism 6 software using unpaired Student's t test or Mann-Whitney test. The two-way Anova test with Bonferroni correction was used for the analysis of tumor growth, the loss of weight and DAI. *, P<0.05; , P<0.01; *, P<0.001; ****, P<0.0001. Normal distribution of the data was assessed using d'Agostino-Pearson omnibus normality test. Error bars represent mean±SEM.

Results

Figure 1B:
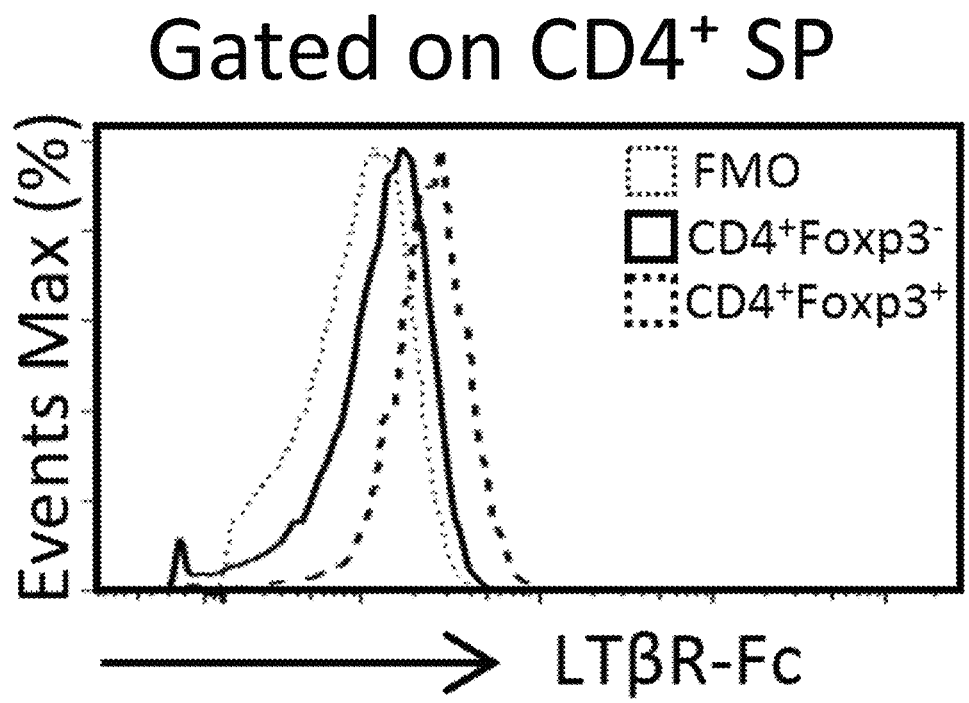
Figure 1C:
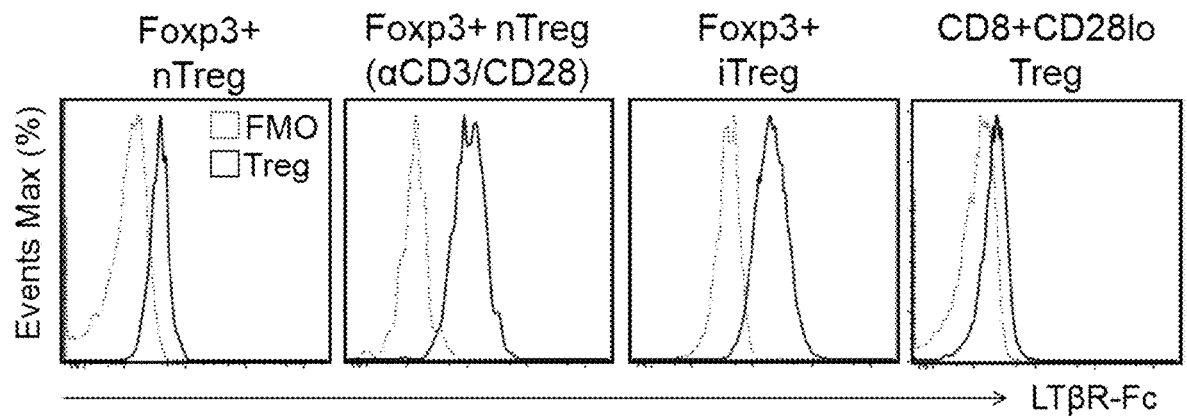

Developing LTα$^{-/-}$ Tregs Exhibit a Signature of Highly Suppressive Cells from their Emergence in the Thymus We and others have previously reported that LTα is upregulated in the thymus upon positive selection in single positive thymocytes and particularly in CD4$^+$ thymocytes by high affinity interactions with medullary thymic epithelial cells. Since Foxp3$^+$ Treg cells are selected by high affinity TCR interactions with thymic stromal cells, we analyzed the expression level of LTα mRNA in purified Tregs from the thymus of Foxp3-GFP reporter mice. Strikingly, we found that CD4$^+$Foxp3$^+$ Tregs express ~5-fold more LTα mRNA than conventional CD4$^+$Foxp3$^-$ T cells (FIG. 1A). Similarly to LTα, LTβ mRNA was also overexpressed in CD4$^+$Foxp3$^+$ Tregs compared to conventional CD4$^+$Foxp3$^-$ T cells. The staining with a soluble LTβR-Fc fusion protein revealed that LTα protein was substantially more expressed in CD4$^+$ Foxp3$^+$ Tregs than in conventional CD4$^+$Foxp3$^-$ T cells, as a membrane anchored LTα1β2 heterocomplex (FIG. 1B), which only binds to LTβR receptor. Natural Treg cell development is a multistage process that leads to the development of Foxp3$^+$CD25$^+$ Tregs from Foxp3$^-$CD25$^+$ and Foxp3$^+$CD25$^-$ cell precursors. Interestingly, LTβR-Fc staining was substantially higher in Foxp3$^+$CD25$^-$ precursors and Foxp3$^+$CD25$^+$ mature Treg cells than in Foxp3$^-$CD25+ precursors, indicating that LTα1β2 expression correlates with that of Foxp3 (data not shown). LTα1β2 expression was conserved in natural Tregs derived from the spleen (FIG. 1C). This expression increased in activated Foxp3$^+$ Tregs with anti-CD3ε/CD28 antibodies. We further examined whether LTα1β2 was expressed in other T-cell subsets endowed with regulatory properties such as induced Foxp3$^+$ Tregs (iTregs) and CD8$^+$CD28$^{lo}$ Tregs. In contrast to CD8$^+$ CD28$^{lo}$ Tregs, we found that the LTα1β2 heterocomplex was highly expressed in Foxp3$^+$ iTregs (FIG. 1B). These data indicate that high levels of LTα1β2 are restricted to the Treg cell lineage expressing the transcription factor Foxp3 and that this expression substantially increases upon TCR activation. This preferential expression in Foxp3+ Tregs compared to conventional CD4$^+$ T cells suggests that LTα could be involved in Treg suppressive activity. We thus analyzed the developmental and functional properties of Foxp3+ Tregs derived from LTα$^{-/-}$ mice.

We observed that LTα$^{-/-}$ mice showed normal frequencies and numbers of Foxp3$^-$CD25$^+$ and Foxp3$^+$CD25$^-$ precursors and Foxp3$^+$CD25$^+$ mature Tregs in their thymi (data not shown). Furthermore, similarly to their WT counterparts, Foxp3$^+$CD25+ thymic Tregs from LTα-/- mice exhibited comparable level of the chemokine receptor CCR7 involved in cortico-medullary migration of single positive thymocytes and were thus preferentially located in the medulla at a normal density (data not shown). Compared to Qa-2$^-$ Foxp3$^+$ newly generated Tregs, Qa-2$^+$Foxp3$^+$ mature Tregs from LTα$^{-/-}$ mice also upregulated the expression of the sphingolipid receptor S1P1 (data not shown), implicated in T-cell egress from the thymus, suggesting that LTα$^{-/-}$ Tregs are normally exported to the periphery. In accordance with this observation, normal frequencies and numbers of recent thymic emigrants Treg cells were observed in the blood and spleen of LTα$^{-/-}$ mice (data not shown).

Figure 1D:
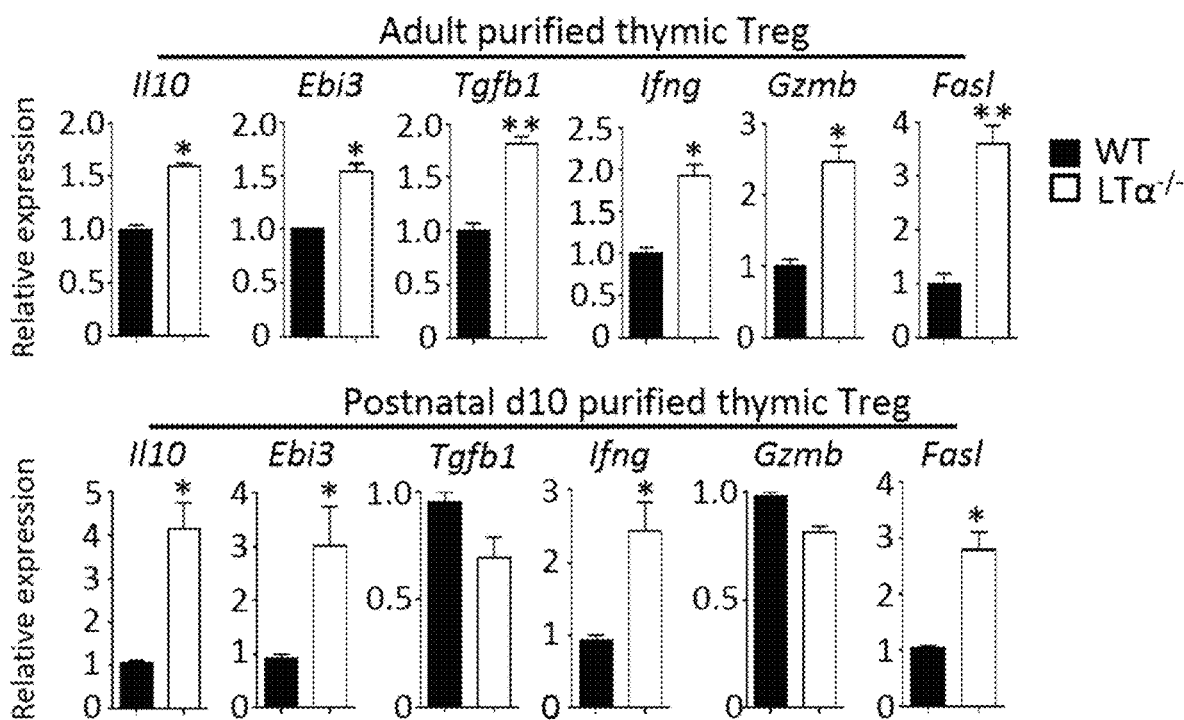

We next investigated the expression level of several genes associated with Treg cell function by qPCR. In adult mice, although CTLA-4, CD39, CD73 and LAG-3 mRNAs showed normal expression levels (data not shown), in contrast, thymic LTα$^{-/-}$ Tregs expressed higher levels of IL-10, Ebi3, TGF-β1, IFN-γ, granzyme b (Gzmb) and FasL mRNAs compared to their WT counterparts (FIG. 1D). We hypothesized that the highly suppressive signature of LTα$^{-/-}$ Tregs could be acquired from the emergence of Treg cells. To verify this and exclude any potential peripheral effects due to Treg recirculation into the adult thymus, we analyzed LTα$^{-/-}$ Tregs during the perinatal period that corresponds to the initial appearance of Tregs in the thymus. Similarly to adult Tregs, we found that levels of several genes associated with Treg suppressive function such as IL-10, Ebi3, IFN-γ and FasL were increased in LTα$^{-/-}$ perinatal Tregs (FIG. 1D). To definitively rule out that this highly immunosuppressive signature could be associated with recirculating Tregs, the expression of the chemokine receptor CCR6 that distinguishes developing from recirculating Tregs was analyzed. Normal frequencies and numbers of CCR6$^-$ developing and CCR6$^+$ recirculating Tregs were observed in LTα$^{-/-}$ mice (data not shown), indicating that these mice do not show a defect in Treg recirculation. Furthermore, the expression of several genes associated with Treg cell function was substantially increased in both purified CCR6$^-$ developing and CCR6$^+$ recirculating LTα$^{-/-}$ Tregs compared to their respective WT counterparts (data not shown), indicating that LTα$^{-/-}$ Tregs show a highly immunosuppressive signature from their development in the thymus.

Similarly to conventional CD4$^+$ T cells, the maturation of CD4$^+$Foxp3$^+$ Tregs upon positive selection is characterized by loss of CD69 and the acquisition of Qa2. We found higher frequencies and numbers of CD69$^-$Qa2$^+$ mature cells in developing CCR6$^-$ Tregs in LTα$^{-/-}$ thymi compared to WT thymi (data not shown). Strikingly, in the CCR6$^-$ developing Treg population, we found that the expression of several genes associated with Treg cell function was specifically increased in CD69$^-$Qa2$^+$ mature Tregs from LTα$^{-/-}$ mice compared to WT mice (data not shown). Altogether, these data show that the expression of LTα negatively controls the suppressive signature of developing Tregs from the Qa-2$^+$ stage.

LTα$^{-/-}$ Tregs Adopt Specialized Differentiation Programs

To gain insights into the suppressive activity of LTα$^{-/-}$ Tregs, we analyzed the molecular signature of LTα$^{-/-}$ splenic Tregs by high-throughput RNA-seq (data not shown). Genes showing a significant variation in gene expression between WT and LTα$^{-/-}$ Tregs (P value≤0.05) and a fold change difference ≥2 and ≤0.5 were considered as up and down-regulated, respectively. We identified a total of 306 upregulated and 113 downregulated genes in LTα$^{-/-}$ Tregs compared to WT Tregs (data not shown). To better characterize the set of genes modulated in LTα$^{-/-}$ Tregs, we performed a Gene Ontology (GO) analysis. Genes overexpressed in LTα$^{-/-}$ Tregs were associated with eight main biological processes (data not shown). The top GO term hit for the set of input genes was associated with cell cycle process and cell proliferation. A heatmap of genes implicated in these categories revealed that many key regulators of cell proliferation were upregulated in LTα$^{-/-}$ Tregs such as Uhrf1, implicated in the proliferation and maturation of colonic Tregs. Consistently with these RNA-seq data, we observed higher frequencies of proliferating Ki-67$^+$ cells in Foxp3$^+$ Tregs from the spleen of LTα$^{-/-}$ mice than in WT mice (data not shown). A heatmap of genes associated with transcription also identified key regulators of this process such as Ahr whose activation was found to induce suppressive Tregs that prevent T-cell induced colitis.

Tregs can adopt specialized differentiation programs that are controlled by several transcription factors that have been associated with helper T cell differentiation. We found that Tbx21, Irf4, Rorc, Bcl6 and Pparγ transcription factors expressed by effector Tregs specialized in controlling Th1, Th2, Th17, CD4 follicular helper effector T cells and fat-resident T cells respectively were strongly upregulated in LTα$^{-/-}$ Tregs (data not shown). This upregulation was also observed in CCR6$^-$ developing and CCR6$^+$ recirculating thymic LTα$^{-/-}$ Tregs (data not shown). Consistently with these observations, many genes reported to be associated with helper T cell polarization were also upregulated in LTα$^{-/-}$ Tregs. Moreover, the transcription factor Blimp-1 (Prdm1 gene) that represents a common signature for all effector Tregs as well as Klrg1 and Tigit that characterize terminally activated and/or differentiated effector Tregs were upregulated in LTα$^{-/-}$ Tregs. In accordance with these data, increased frequencies of KLRG1$^+$ cells and CD69$^+$CD44$^+$ effector cells were observed in CD4$^+$Foxp3$^+$ Tregs from the spleen of LTα$^{-/-}$ mice (data not shown). Furthermore, we found that LTα$^{-/-}$ Tregs express higher levels of CD44, Helios and Nur77 activation markers by flow cytometry (data not shown).

RNA-seq data also revealed that LTα$^{-/-}$ Tregs expressed abundant amounts of mRNAs encoding for several genes associated with immunosuppressive functions of Tregs such as Ebi3, Il10, Tgf-β and Gzmb. Consistently with these observations, in contrast to CD69-CD44$^+$ Treg cells, several genes associated with Treg effector functions such as Il10, Ebi3, Tgfb, Ifng, Gzmb and Fas1 were specifically upregulated in CD69$^+$CD44$^+$ effector Treg cells at high levels in LTα$^{-/}$ mice (data not shown). Similarly to thymic Tregs (data not shown), the expression of other genes associated with Treg effector functions such as Ctla4, CD39, CD73 and Lag3 were unchanged in splenic LTα$^{-/-}$ Tregs (data not shown). Importantly, the expression of several candidate genes in the distinct categories identified by RNA-seq analysis was confirmed by qPCR on purified WT and LTα$^{-/-}$ Tregs (FIG. 2). Altogether, these data thus show that LTα$^{-/-}$ Tregs are polarized and thus exhibit an activated/effector phenotype.

The Adoptive Transfer of LTα$^{-/-}$ Tregs Protects from Ulcerative Colitis

Figure 3A:
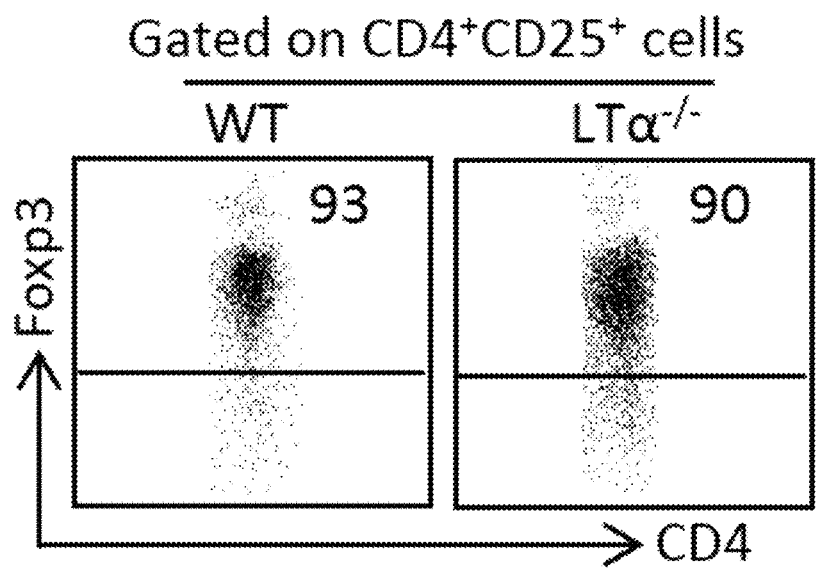
Figure 3B:
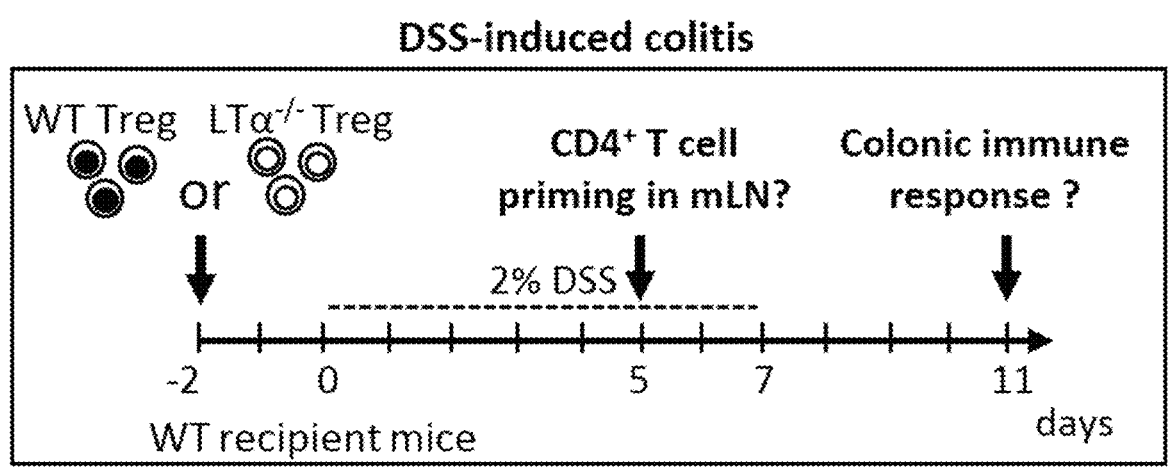
Figure 3C:
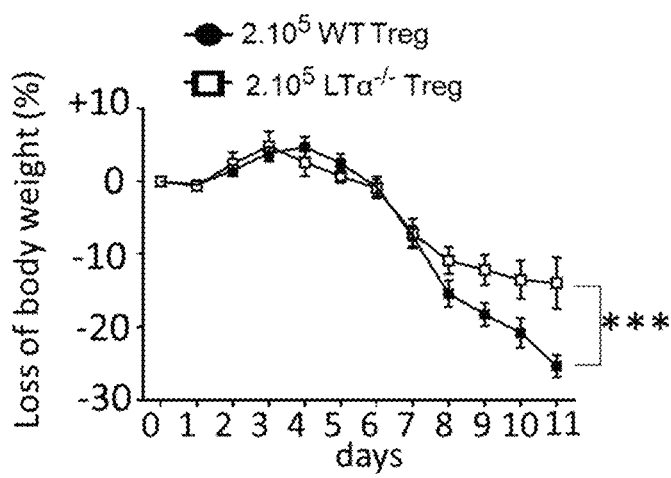
Figure 3D:
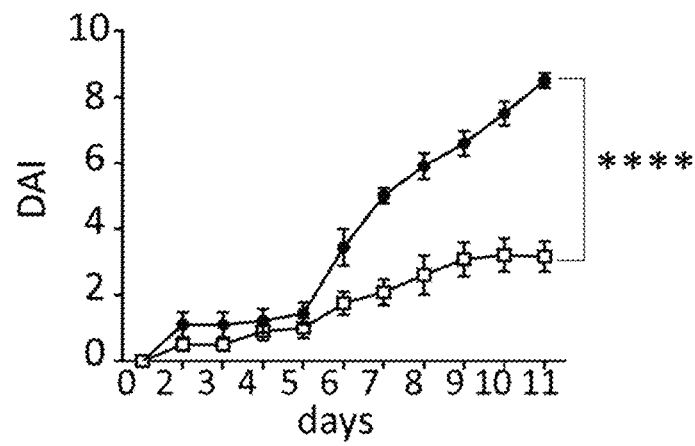
Figure 3E:
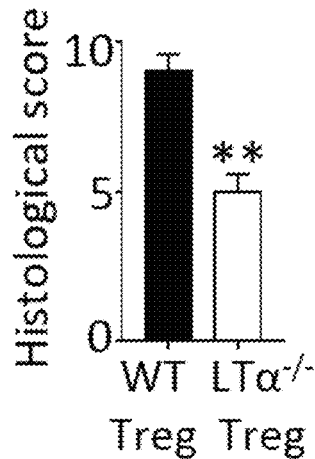
Figure 3F:
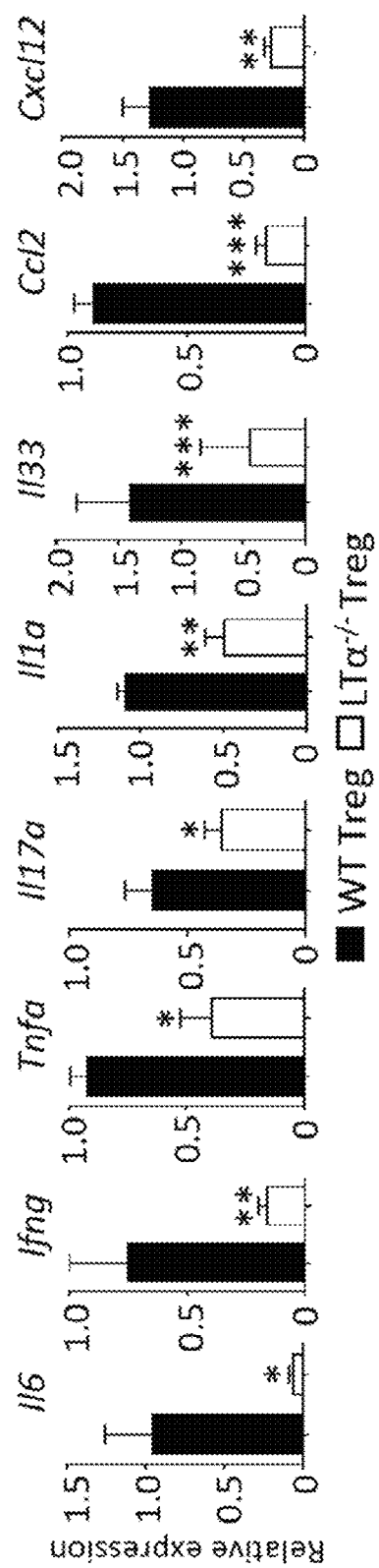
Figure 3G:
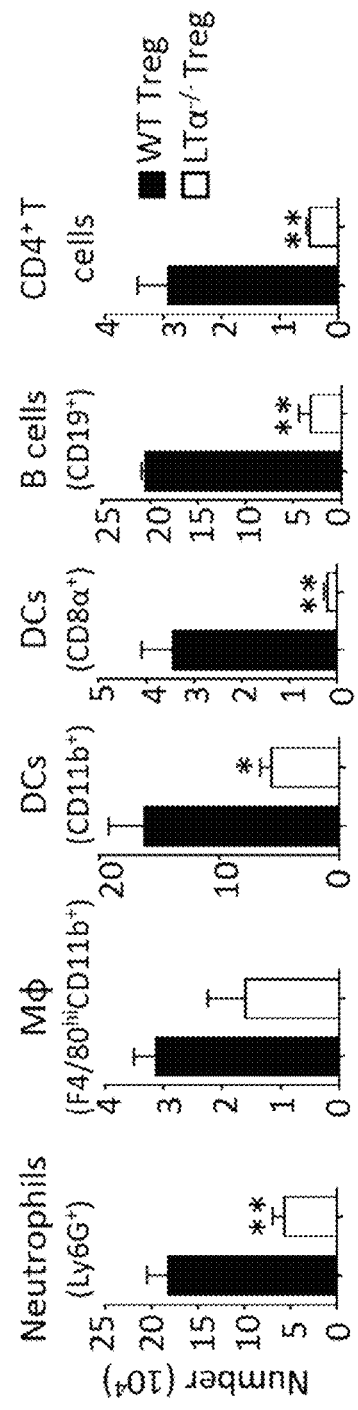
Figure 3H:
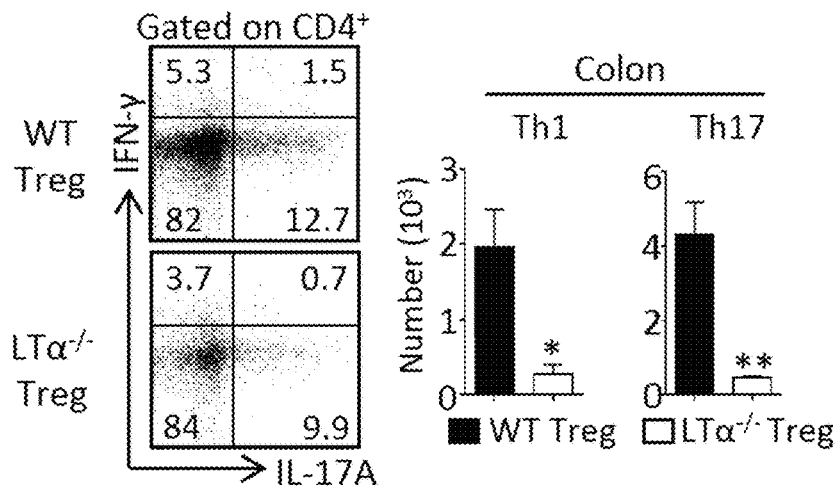
Figure 3I:
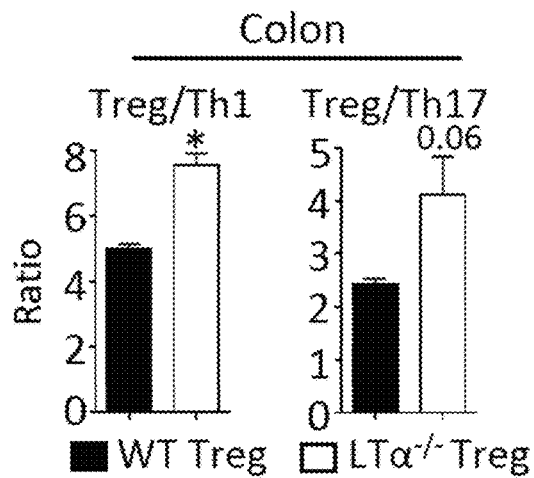
Figure 3J:
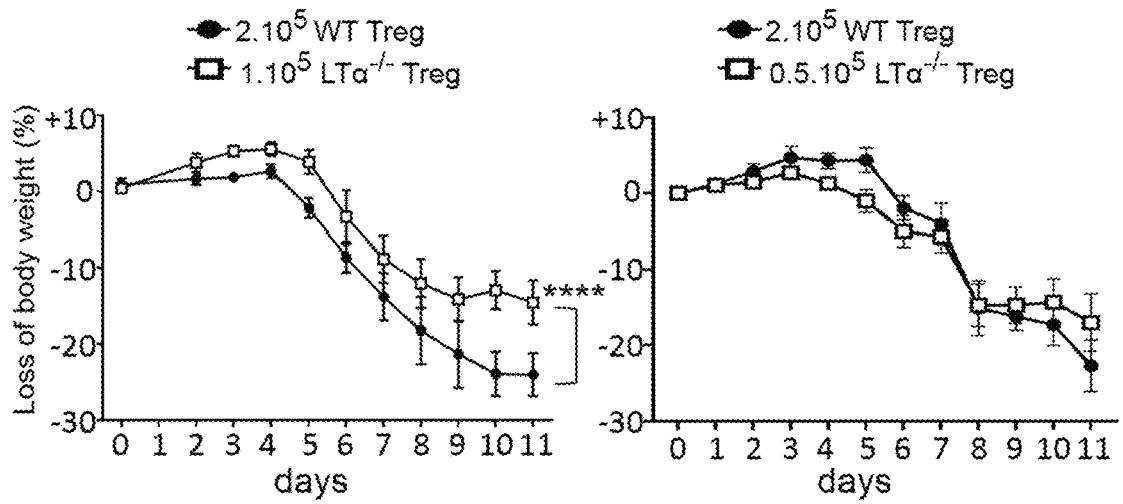

Given that LTα$^{-/-}$ Tregs highly express several genes implicated in Treg suppressive functions (FIGS. 1D and 2), we next evaluated whether the adoptive transfer of LTα$^{-/-}$ Tregs shows therapeutic benefits to protect from dextran sodium sulfate (DSS)-induced colitis. 2·10$^5$ CD4$^+$CD25$^+$ cells that predominantly contain Foxp3$^+$ Tregs (FIG. 3A) purified from WT or LTα$^{-/-}$ mice were injected into WT recipient mice two days before the induction of colitis with 2% DSS (FIG. 3B). We observed that mice injected with LTα$^{-/-}$ Tregs lost significantly less weight than those injected with WT Tregs (FIG. 3C). Moreover, the disease activity index (DAI), which combines stool consistency, rectal bleeding and weight loss was substantially less important in these mice (FIG. 3D). In accordance with the weight loss and DAI, these mice displayed less damages of the colonic epithelium (data not shown) and a reduced colitis histological score at the end of the experiment (FIG. 3E). We also observed a reduced expression of pro-inflammatory cytokines such as Il6, Ifnγ, Tnf-α, Il17A, Il1α and Il33 as well as of chemokines implicated in the recruitment of immune cells such as Ccl2 and Cxcl12 in colons of mice transferred with LTα$^{-/-}$ Tregs (FIG. 3F). We further analysed the nature of colon-infiltrating immune cells by flow cytometry. Numbers of neutrophils, macrophages, dendritic cells, B cells and CD4$^+$ T cells were drastically reduced in mice transferred with LTα$^{-/-}$ Tregs compared to those transferred with WT Tregs (FIG. 3G). A reduced infiltration of CD3+ and B220+ cells was confirmed on histological colon sections (data not shown). Numbers of Th1 and Th17 effector CD4+ T cells were also reduced (FIG. 3H). Consequently, Treg/Th1 and Treg/Th17 ratios were increased in the colon of mice transferred with $LT\alpha^{-/-}$ Tregs (FIG. 3I). We then assessed the potential of $Lt\alpha^{-/-}$ Tregs to protect against colitis by reducing the number of adoptively transferred cells from $2 \cdot 10^5$ to $1 \cdot 10^5$ and then to $0.5 \cdot 10^5$ cells. We observed that $1 \cdot 10^5$ Tregs still shows a better protection than $2 \cdot 10^5$ WT Tregs characterized by reduced weight loss (FIG. 3J). Interestingly, $0.5 \cdot 10^5$ Tregs show the same protective effect than $2 \cdot 10^5$ WT Tregs, indicating that $Lt\alpha^{-/-}$ Tregs are ~4 times more suppressive in vivo than their WT counterparts.

We next further determined whether the adoptive transfer of $LT\alpha^{-/-}$ Tregs inhibits CD4+ T cell priming in mesenteric lymph nodes five days after the administration of DSS. Of note, we found that mice injected with $LT\alpha^{-/-}$ Tregs already showed longer colon length and reduced colonic weight/length ratio at this time point, indicative of attenuated colon inflammation (data not shown). Strikingly, numbers of Th1 and Th17 effector CD4+ T cells were substantially reduced in mesenteric lymph nodes of these mice (data not shown), indicating that $LT\alpha^{-/-}$ Tregs inhibit the conversion of naïve CD4+ T cells into effectors. Altogether, these data show that the adoptive transfer of $LT\alpha^{-/-}$ Tregs protects from the development of ulcerative colitis by dampening colon inflammation and the priming of pathogenic CD4+ T cells in mesenteric lymph nodes.

Figure 4A:
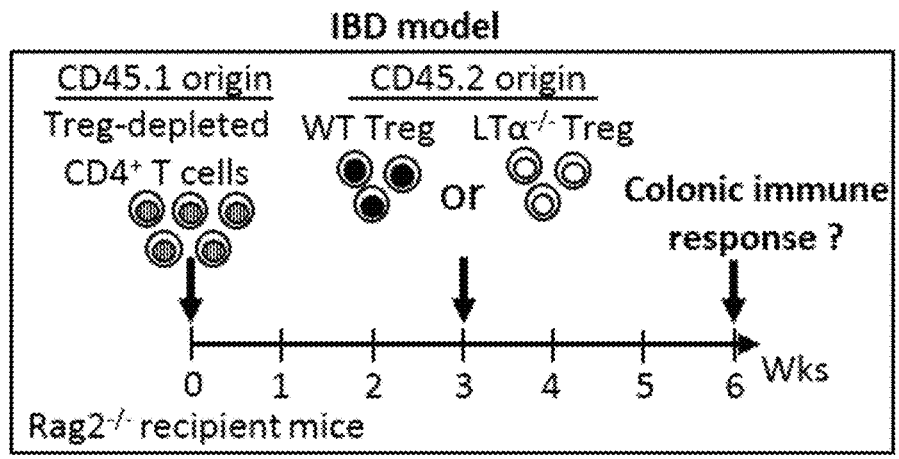
Figure 4B:
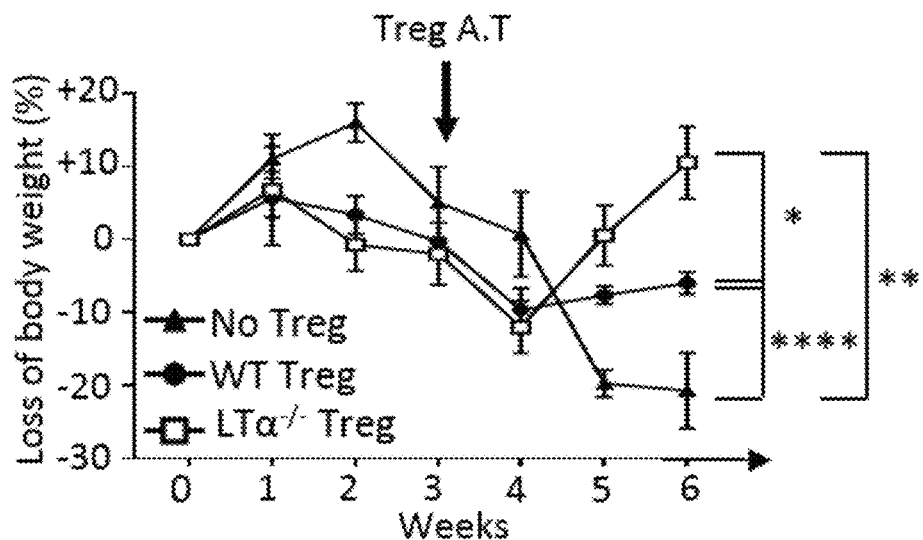
Figure 4C:
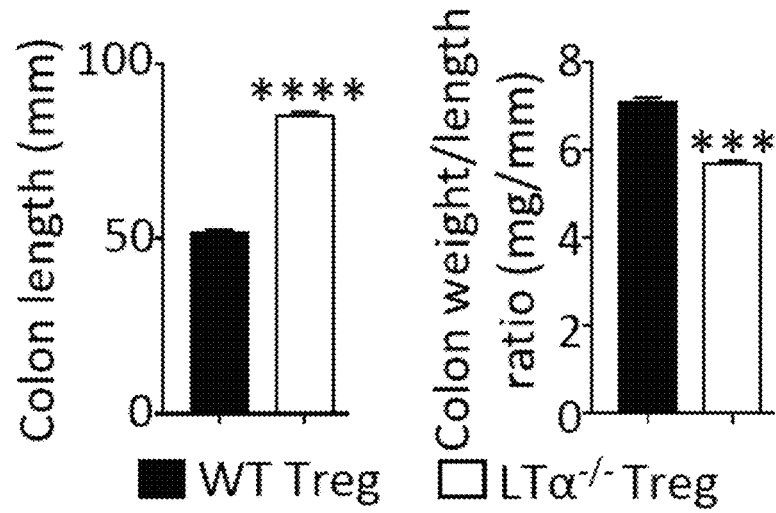
Figure 4D:
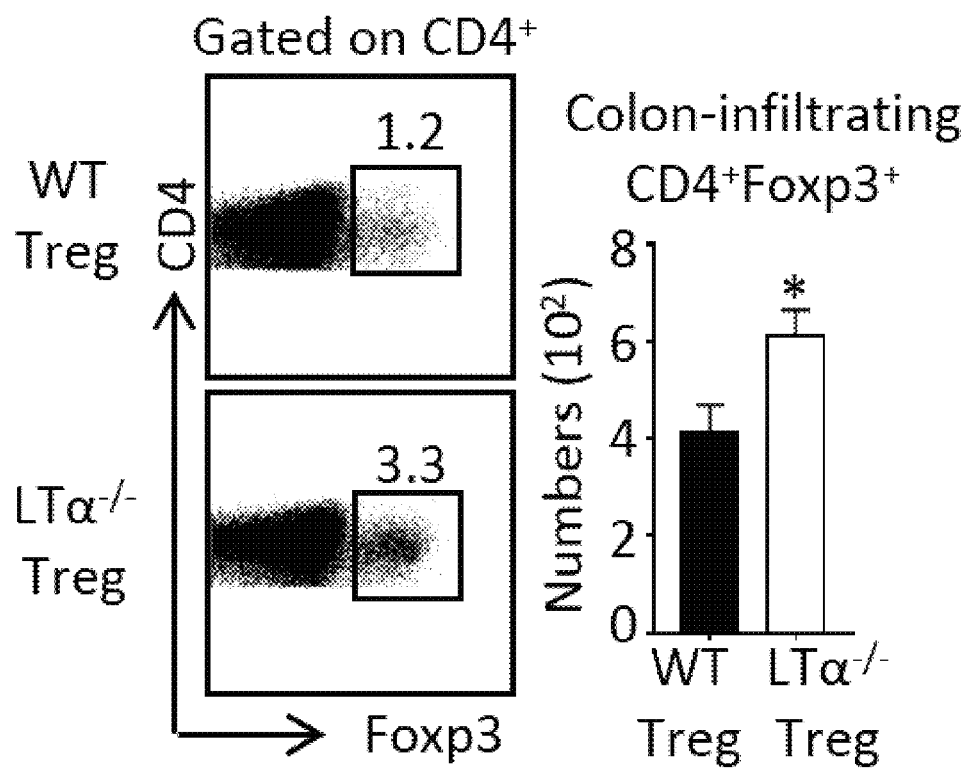
Figure 4E:
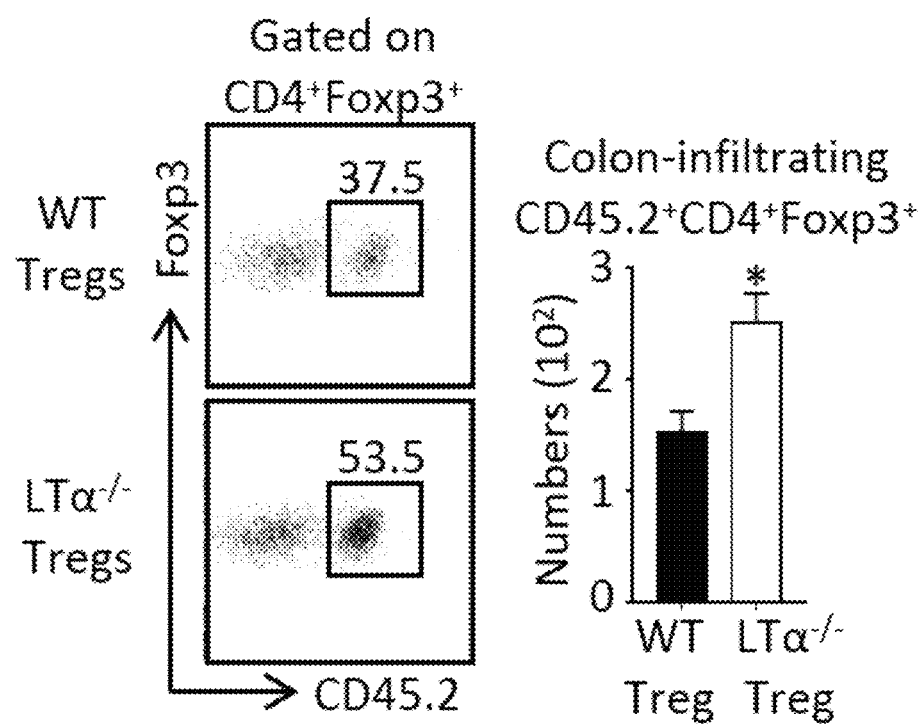
Figure 4F:
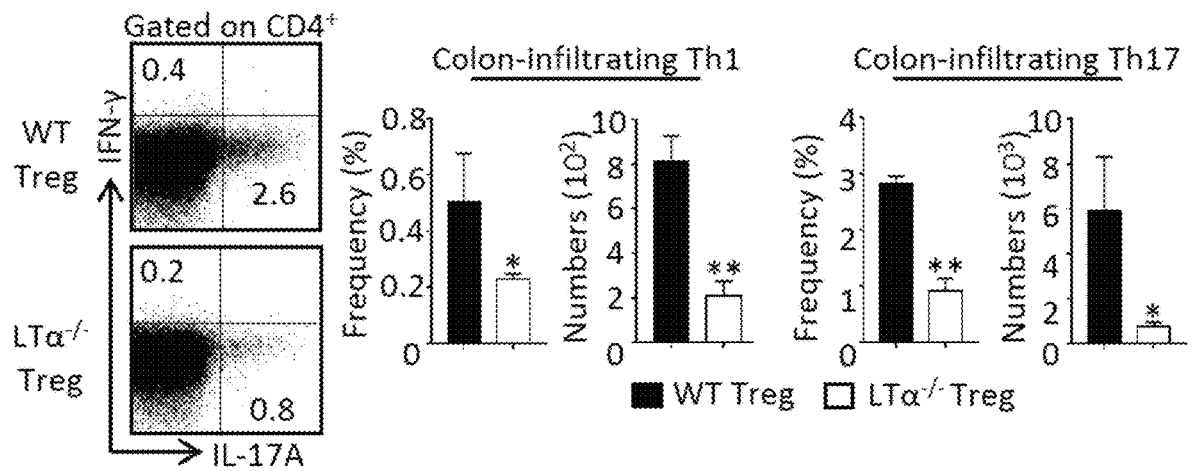
Figure 4G:
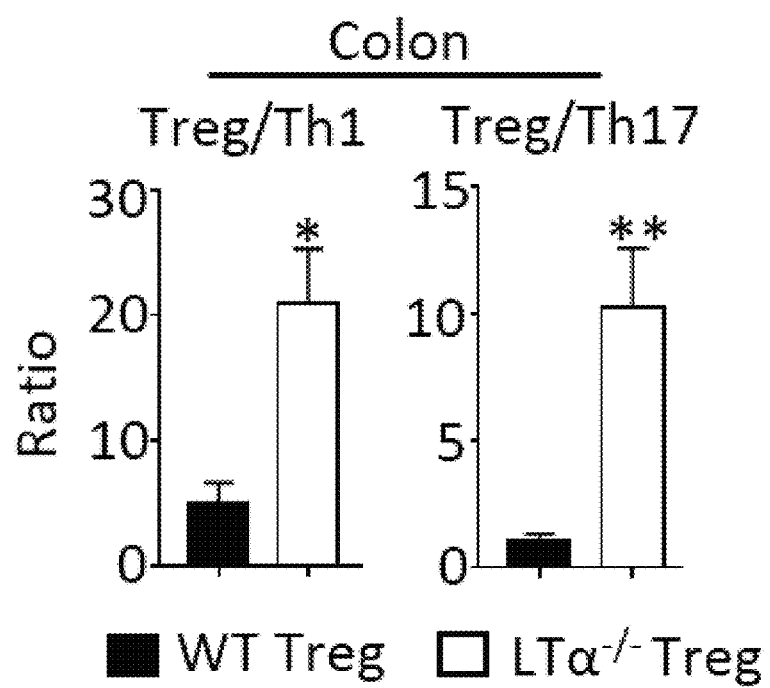

The Adoptive Transfer of $LT\alpha^{-/-}$ Tregs Promotes the Recovery from Inflammatory Bowel Disease We next investigated whether the adoptive transfer of $LT\alpha^{-/-}$ Tregs could show benefits to cure inflammatory bowel disease (IBD). To address this issue, IBD was induced by transfer of CD4+CD25+ Treg-depleted naïve CD4+ T cells from CD45.1 WT congenic mice into Rag2−/− recipient mice and the development of IBD was monitored by assessing weight loss. Around 3 to 4 weeks after T cell adoptive transfer, when mice developed clinical symptoms of IBD characterized by diarrhea and weight loss, they received purified WT or $LT\alpha^{-/-}$ Tregs and body weight was monitored once per week (FIG. 4A). Mice that did not receive Tregs were used as controls. Mice transferred with WT Tregs gained more weight than mice that did not receive Tregs, indicating that the transfer of WT Tregs ameliorates IBD (FIG. 4B). Interestingly, mice that were transferred with $LT\alpha^{-/-}$ Tregs gained more weight than mice that received WT Tregs. Strikingly, these mice showed a higher colon length with a reduced colonic weight/length ratio, indicative of attenuated colon inflammation (FIG. 4C). In accordance with these observations, these mice exhibited a reduced histological score (data not shown). Importantly, numbers of total Foxp3+ Tregs and Foxp3+ Tregs of CD45.2 origin were more elevated in the colon of mice transferred with $LT\alpha^{-/-}$ Tregs than those injected with WT Tregs (FIG. 4D-E). Furthermore, numbers of Th1 and Th17 effector CD4+ T cells were reduced in the colon of these mice (FIG. 4F). Consequently, Treg/Th1 and Treg/Th17 ratios were increased in these mice (FIG. 4G). Of note, in this experimental setting we observed that frequencies and numbers of CD4+ T cells were reduced in several peripheral tissues such as salivary glands, pancreas and lung, indicating that $LT\alpha^{-/-}$ Tregs also control tissue infiltration of autoreactive CD4+ T cells (data not shown). Furthermore, numbers of $CD44^{hi}CD62L^{hi}$ central and $CD44^{hi}CD62L^{lo}$ effector memory CD4+ T cells were specifically reduced in these peripheral tissues (data not shown). Altogether, these data demonstrate that the adoptive transfer of $LT\alpha^{-/-}$ Tregs is able to treat IBD and controls tissue infiltration of autoreactive CD4+ T cells.

Figure 5A:
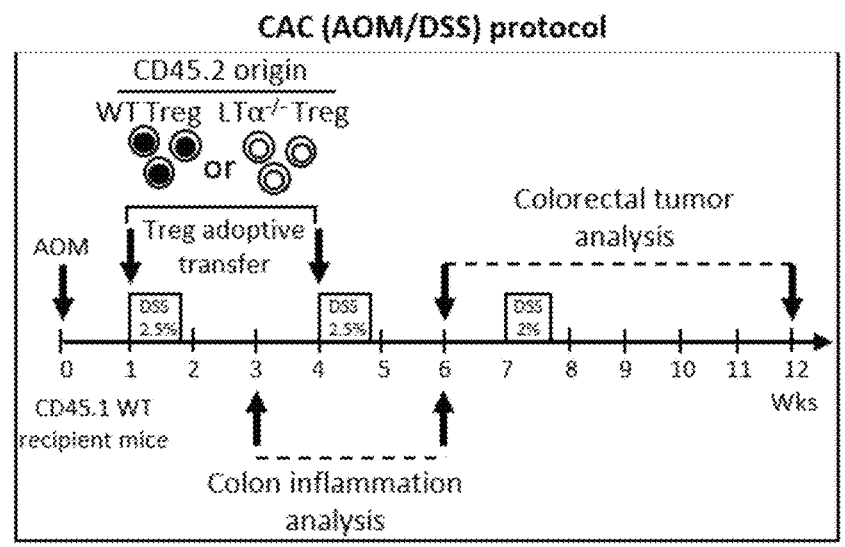
Figure 5B:
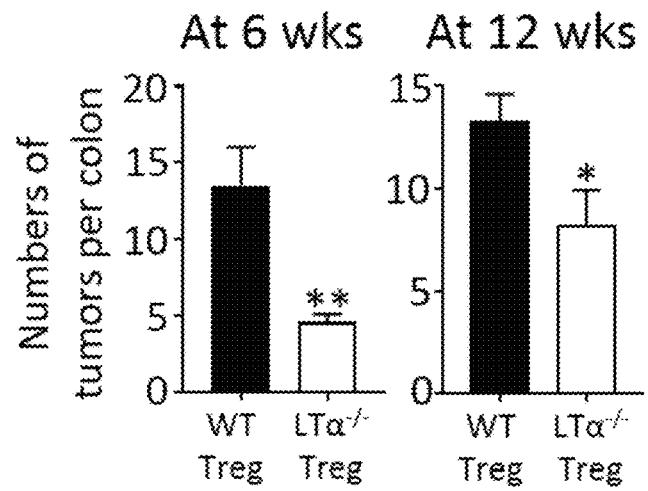
Figure 5C:
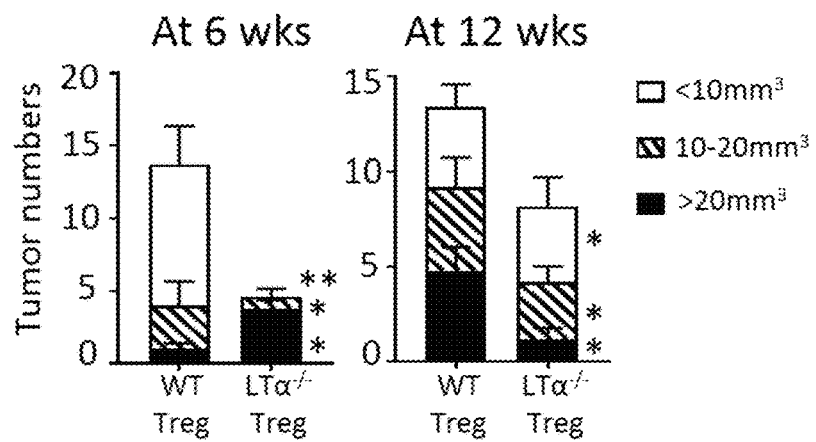
Figure 5D:
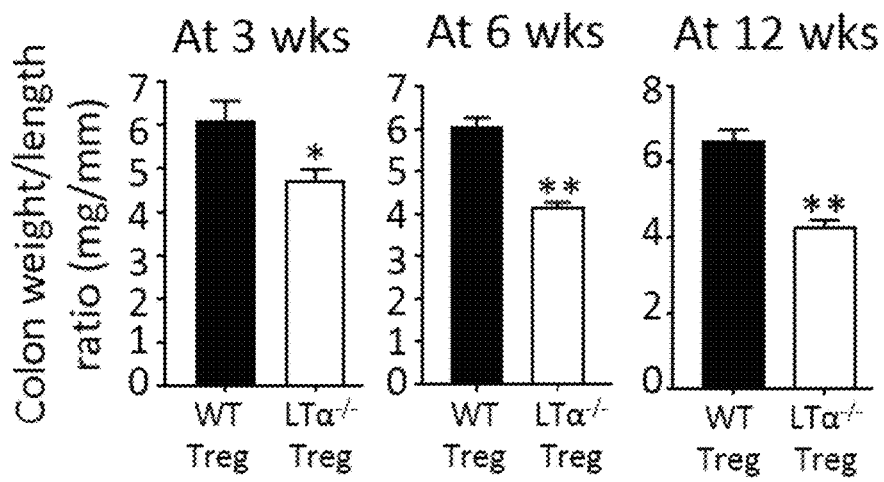
Figure 5E:
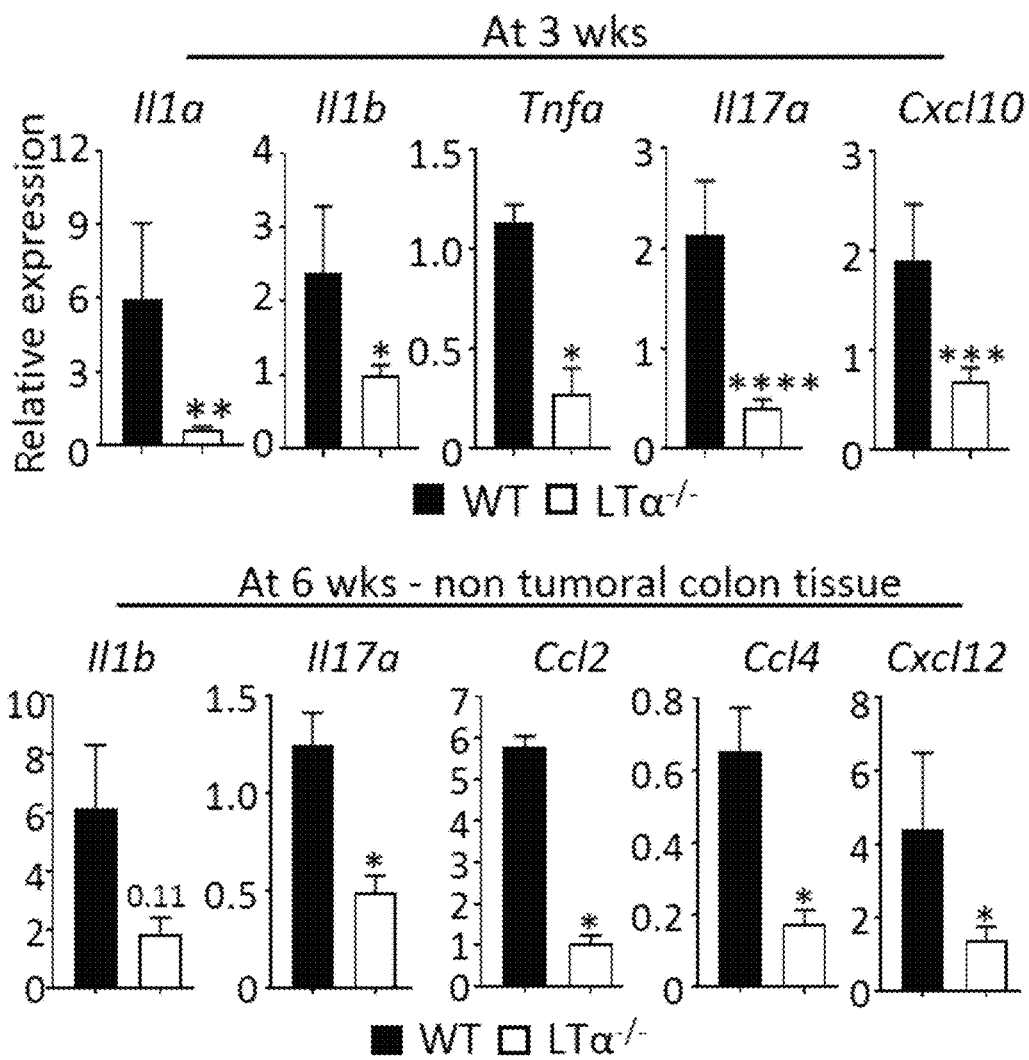
Figure 5F:
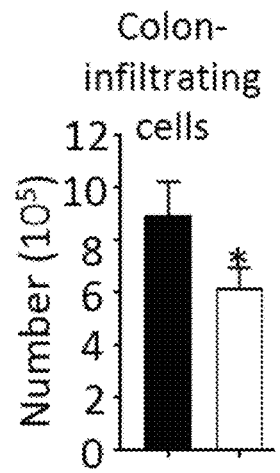
Figure 5G:
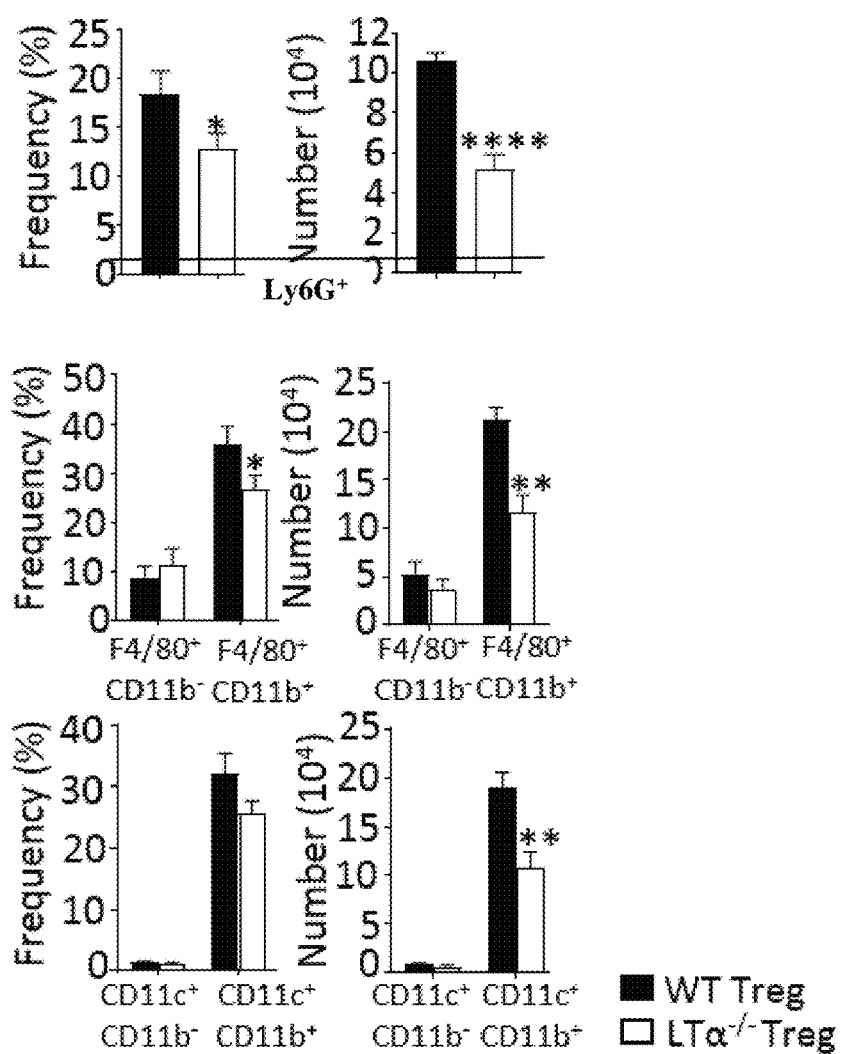
Figure 5H:
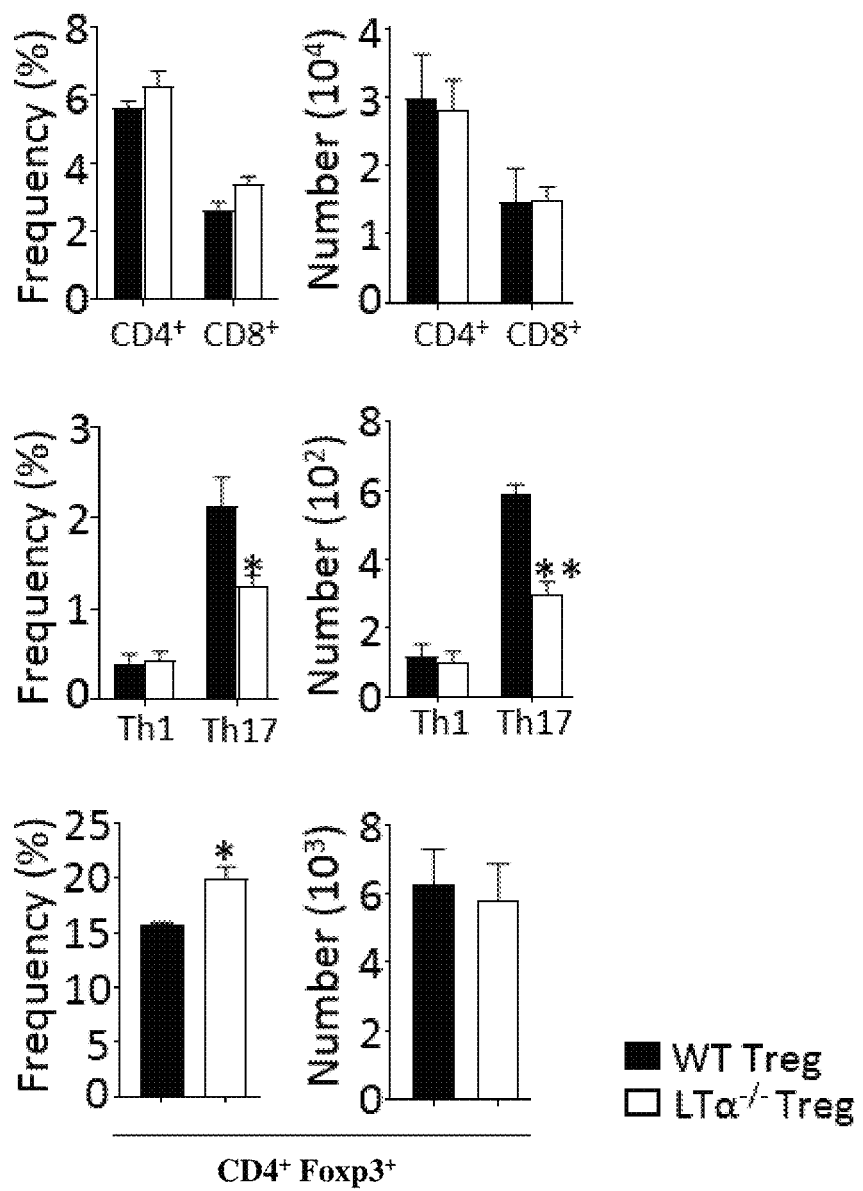

The Adoptive Transfer of $LT\alpha^{-/-}$ Tregs Attenuates the Development of CAC Given that $LT\alpha^{-/-}$ Tregs protect from DSS-induced colitis (FIG. 3) and that colon chronic inflammation can result in the initiation of CAC, we next evaluated whether the adoptive transfer of $LT\alpha^{-/-}$ Tregs protects from the emergence of CAC. For this, we used a classical CAC protocol that consists in the administration of azoxymethane (AOM), initiating tumorigenesis followed by three cycles of DSS, inducing a chronic colitis, which promotes the development of multiple colorectal tumors (FIG. 5A). These repetitive cycles of DSS mimic active and remission phases of colon inflammation observed in patients. $LT\alpha^{-/-}$ Tregs were adoptively transferred before the two first cycles of DSS, period that corresponds to the CAC inflammation phase that precedes the development of colorectal tumors. Interestingly, mice that received $LT\alpha^{-/-}$ Tregs showed fewer colorectal tumors, mainly located in the distal colon, with a globally reduced volume than mice transferred with WT Tregs at both 6 and 12 weeks of the CAC protocol (FIGS. 5B-C and data not shown). We thus hypothesized that the development of colorectal tumors is prevented by reduced colon inflammation in mice transferred with $LT\alpha^{-/-}$ Tregs. Consistently, these mice show a reduced colonic weight/length ratio from 3 weeks until the end of the protocol, indicative of an attenuated colon inflammation (FIG. 5D). At 3 weeks of the CAC protocol, we observed a reduced expression of pro-inflammatory cytokines such as Il1α, Il1β, Tnf-α and Il17A in the colon of mice injected with $LT\alpha^{-/-}$ Tregs (FIG. 5E). Reduced expression of pro-inflammatory cytokines also persisted at 6 weeks of the CAC protocol. Furthermore, the expression of chemokines implicated in the recruitment of immune cells such as Ccl2, Ccl4, Cxcl10 and Cxcl12 were also reduced in colons of these mice (FIG. 5E). We next examined the nature of colon infiltrating inflammatory immune cells by flow cytometry at 3 weeks of the CAC protocol (FIG. 5F-H). Numbers of total colon infiltrating immune cells was substantially reduced in mice transferred with $LT\alpha^{-/-}$ Tregs compared to those transferred with WT Tregs (FIG. 5F). Numbers of neutrophils, macrophages and dendritic cells were specifically reduced in the colon of these mice (FIG. 5G). Furthermore, while numbers of CD4+ and CD8+ T cells were similar in the colon of both groups, numbers of Th17 effector CD4+ T cells were specifically reduced in mice that received $LT\alpha^{-/-}$ Tregs (FIG. 5H). In contrast, frequencies of colon-infiltrating Foxp3+ Tregs were increased in these mice although their numbers were similar to those observed in mice transferred with WT Tregs. Altogether, these data show that the adoptive transfer of $LT\alpha^{-/-}$ Tregs during colon chronic inflammation attenuates the development of colorectal tumors by dampening colon inflammation.

The Adoptive Transfer of $Lt\alpha^{-/-}$ Tregs Limits Multi-Organ Autoimmunity

We next evaluated the ability of $Lt\alpha^{-/-}$ Tregs to limit multi-organ autoimmunity in a model of wasting disease. CD4+CD25+ Treg-depleted total splenocytes isolated from CD45.1 WT congenic mice were transferred into $Rag2^{-/-}$ recipients. Four weeks later, when mice lost weight they received purified WT or $Lt\alpha^{-/-}$ Tregs and body weight was monitored once per week (FIG. 6A). Mice that received concomitantly CD4+CD25+ Treg-depleted total splenocytes and WT Tregs at the beginning of the experimental protocol were used as controls. Interestingly mice transferred with Ltα$^{-/-}$ Tregs gained more weight than mice that received WT Tregs (FIG. 6B). Importantly, these mice regained around 15% of their initial weight, almost reaching the weight of controls at the end of the protocol. Three weeks after Treg adoptive transfer, in contrast to mice that received WT Tregs, showing elevated numbers of splenic CD4$^+$ and CD8$^+$ T cells of CD45.1 origin, mice transferred with Ltα$^{-/-}$ Tregs had similar numbers of these cells than those observed in controls (data not shown). Moreover, splenic CD4$^+$ and CD8$^+$ donor T cells contained less CD44$^+$CD62L$^-$ activated cells in mice transferred with Ltα$^{-/-}$ Tregs compared to mice injected with WT Tregs, indicating that Ltα$^{-/-}$ Tregs attenuate T cell activation (data not shown). Similarly to controls, a reduced infiltration of inflammatory cells was observed by histological examinations in peripheral tissues, including the salivary glands and pancreas in mice transferred with Ltα$^{-/-}$ Tregs compared to mice that received WT Tregs (data not shown). Accordingly, the examination of CD45.1 donor cell infiltration by flow cytometry in individual mice revealed a lower infiltration in the salivary glands, pancreas and kidney of mice transferred with Ltα$^{-/-}$ Tregs (FIG. 6C). We took advantage of this setup based on the adoptive transfer of Treg-depleted total splenocytes (FIG. 6A) to assess the generation of autoantibodies against several peripheral organs. Immunostaining of Rag2$^{-/-}$ tissue sections with sera from the three groups of mice revealed that serum from mice transferred with Ltα$^{-/-}$ Tregs contained less autoantibodies against salivary glands, pancreas, kidney, liver and lung than the serum of mice injected with WT Tregs (data not shown). Thus, the adoptive transfer of Ltα$^{-/-}$ Tregs limits immune cell infiltrations and the generation of autoantibodies against several peripheral tissues.

Adoptively Transferred LTα$^{-/-}$ Tregs Maintain their Highly Immunosuppressive Signature In Vivo Since Treg cells can show a certain plasticity, we analysed the stability of LTα$^{-/-}$ Tregs in vivo upon adoptive transfer. For this, sublethally irradiated CD45.1×CD45.2 WT recipient mice were transferred with the same ratio of cell-sorted CD4$^+$CD25$^+$ WT and LTα$^{-/-}$ Tregs of CD45.1 and CD45.2 origin, respectively (data not shown). One week after adoptive transfer, we purified CD4$^+$CD25$^+$ Tregs of both origins from the spleen of recipient mice (data not shown) and analysed the expression of several genes associated with Treg function. Similar frequencies and numbers of CD4$^+$CD25$^+$ cells of CD45.1 or CD45.2 origins were recovered (data not shown). However, LTα$^{-/-}$ Tregs of CD45.2 origin expressed high levels of Klrg1, Il10, Tgfb, Ifng, gzmb and IL17a (data not shown), indicating that LTα$^{-/-}$ Tregs retained their highly immunosuppressive signature upon adoptive transfer.

LTα Expression in Hematopoietic Cells and LTα1β2/LTβR Axis Negatively Control the Suppressive Signature of Treg Cells Because LTα$^{-/-}$ mice show a disorganized thymic and splenic microenvironment, we first analysed the contribution of non-hematopoietic stromal cells in the highly immunosuppressive phenotype of LTα$^{-/-}$ Tregs. For this, we generated bone marrow (BM) chimeras in which lethally irradiated CD45.2 WT or LTα$^{-/-}$ recipient mice were reconstituted with WT BM cells from CD45.1 congenic mice (WT CD45.1: WT and WT CD45.1: LTα$^{-/-}$ mice, respectively). Six weeks after BM transplantation, CD4$^+$CD25$^+$ Treg cells of CD45.1 donor origin were cell-sorted from the spleen and analysed for the expression of several genes associated with Treg effector function (data not shown). Similar frequencies and numbers of Foxp3$^+$ Tregs were observed in both groups of mice (data not shown). Furthermore, the expression of Klrg1, Tgfb, Gzmb, Fas1 and IL17a was similar in both groups of mice, indicating that non-hematopoietic cells are not implicated in the highly suppressive signature of Tregs observed in LTα$^{-/-}$ mice (data not shown).

Figure 7A:
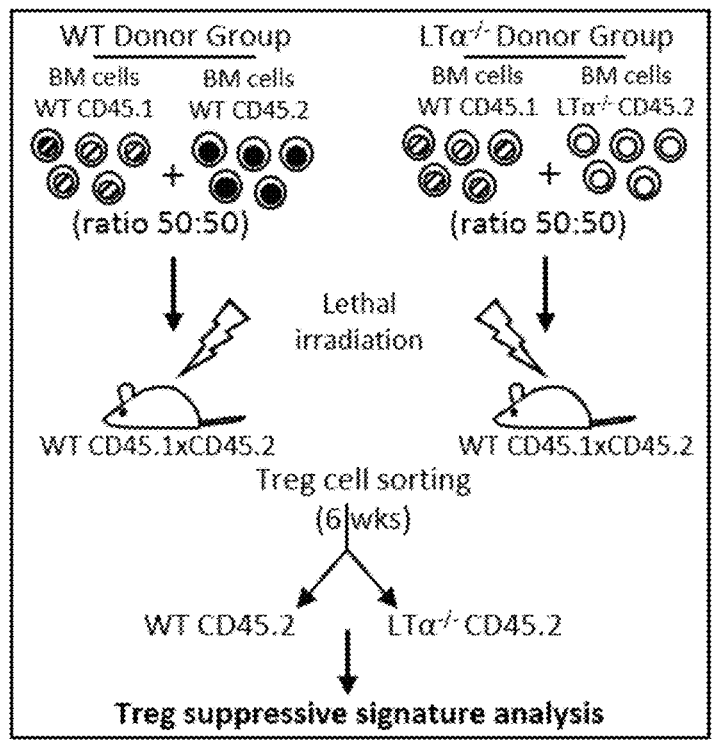
Figure 7B:
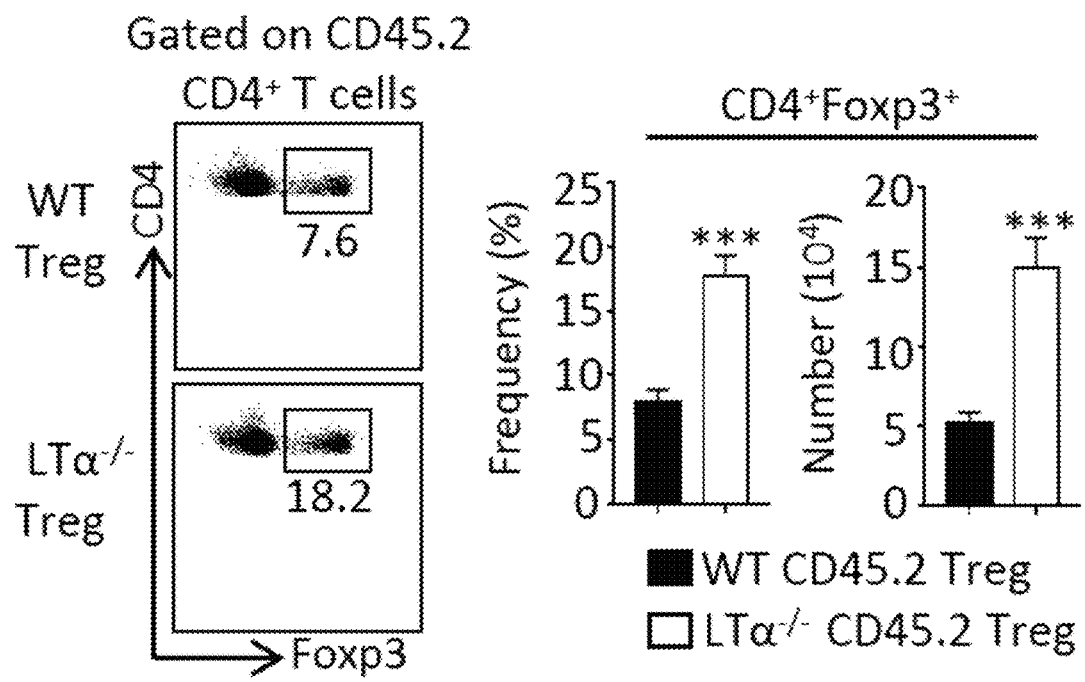
Figure 7C:
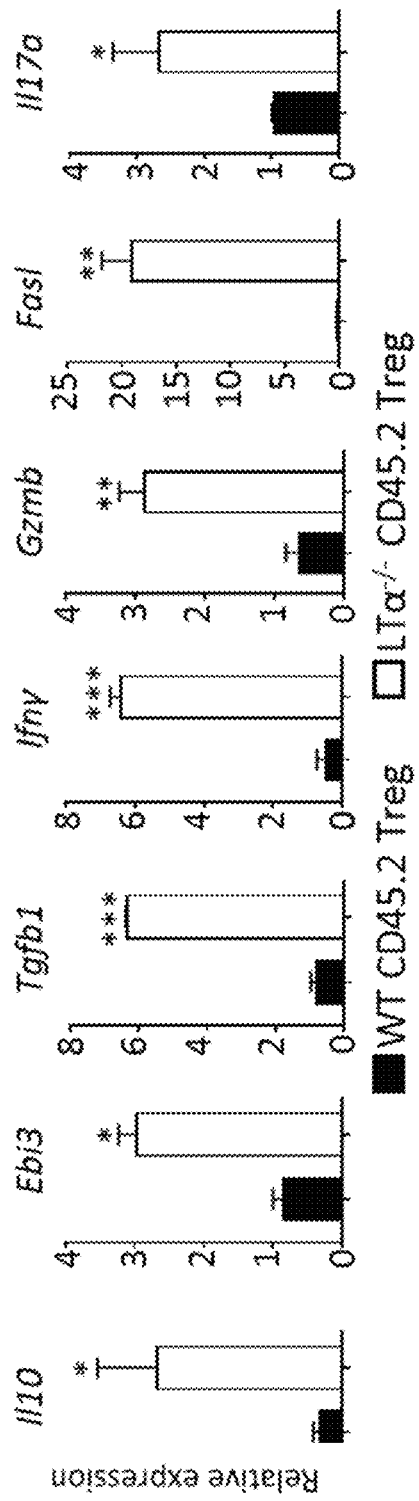

We next determined the respective contribution of the hematopoietic compartment by generating mixed bone marrow chimaeras in which lethally irradiated CD45.1×CD45.2 WT recipient mice were reconstituted with BM cells (50:50) from WT CD45.1 and WT CD45.2 (WT donor group), or WT CD45.1 and LTα$^{-/-}$ CD45.2 (LTα$^{-/-}$ donor group) (FIG. 7A). Six weeks later, we found increased frequencies and numbers of CD4$^+$Foxp3$^+$ Tregs derived from LTα$^{-/-}$ CD45.2 BM cells compared to those derived from WT CD45.2 BM cells in the spleen (FIG. 7B). Strikingly, purified LTα$^{-/-}$ CD45.2 Tregs showed increased expression of Il10, Ebi3, Tgfb1, Ifng, Gzmb, Fas1 and IL17a genes compared to WT CD45.2 Tregs (FIG. 7C). These data indicate that the expression of LTα in hematopoietic cells negatively controls the immunosuppressive signature of Treg cells.

Figure 7D:
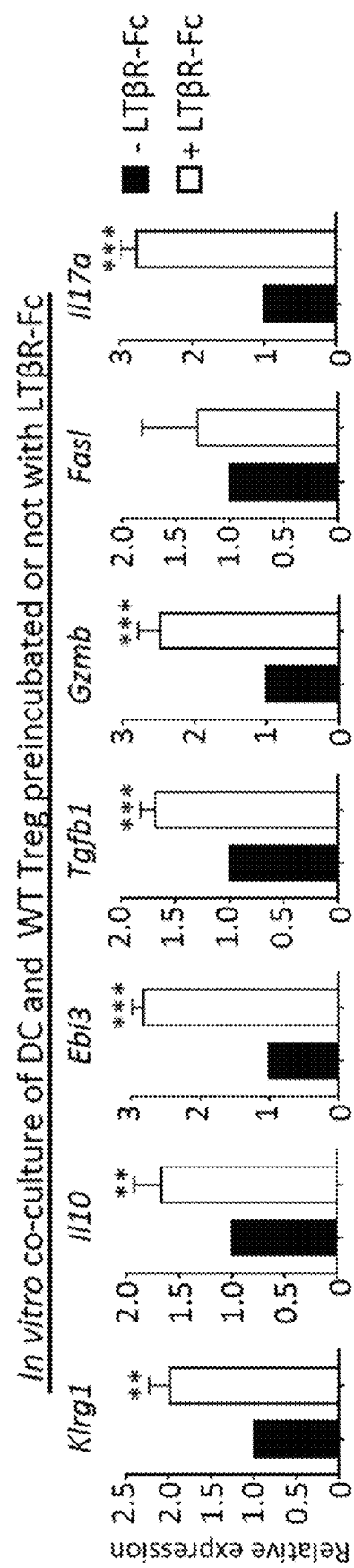

Since we observed that Tregs express LTα, as a membrane anchored LTα1β2 heterocomplex (FIG. 1), we assessed the contribution of LTα1β2/LTβR axis in controlling the suppressive signature of Tregs. In particular, we analyzed whether blocking LTα1β2/LTβR interactions between Tregs and dendritic cells impacts the suppressive signature of Treg cells. For this, purified WT CD4$^+$CD25$^+$ Tregs pre-incubated or not with a soluble LTβR-Fc fusion protein were co-cultured with purified CD11c$^+$ dendritic cells. Interestingly, Tregs that were pre-incubated with LTβR-Fc upregulated the expression of several genes associated with Treg suppressive function such as Klrg1, Il10, Ebi3, Tgfb1, Gzmb, Fas1 and Il17a compared to un-pre-treated Tregs (FIG. 7D). These data thus indicate that LTα1β2/LTβR interactions between Tregs and dendritic cells negatively regulate the suppressive signature of Tregs.

LTα Expression is Conserved in Human Tregs Derived from Peripheral Blood

We next assessed whether LTα expression is conserved in human Tregs derived from peripheral blood of female and male healthy donors. Foxp3$^+$CD4$^+$ Tregs were classically identified as CD4$^+$CD25$^+$CD127$^{lo}$ cells. Intracellular LTα protein (FIG. 8A) and the cell-surface LTα1β2 heterocomplex (FIG. 8B) were substantially detected by flow cytometry in Tregs of all donors analyzed, indicating that this expression is conserved in mice to human.

Discussion

Several studies have identified numerous molecules implicated in the positive regulation of Treg cell development and function. In contrast, few reports have described signals that negatively regulate Treg function. Here, by analyzing distinct T cell populations endowed with regulatory properties, we found that Foxp3$^+$ Tregs substantially express Ltα, as a membrane anchored LTα1β2 heterocomplex. LTα is expressed in Foxp3$^+$ Treg cells, from their development in the thymus at the CD25-Foxp3$^+$ precursor stage. This expression is conserved in peripheral CD25$^+$Foxp3$^+$ Tregs. Similarly to LTβR$^{-/-}$ mice, LTα$^{-/-}$ mice do not show any obvious defect in CD4$^+$Foxp3$^+$ Treg cell development in the thymus. However, the signature of genes associated with suppressive functions was greatly enhanced both in thymic and peripheral LTα$^{-/-}$ Tregs, indicating that LTα negatively regulates their immunosuppressive signature. Our data show that this phenotype is detectable from the development of Tregs in the thymus since this highly suppressive signature was observed from their emergence of this cell type at the perinatal period and in developing CCR6⁻ Treg cells in the adult. This phenotype is thus likely not due to recirculating peripheral Tregs but is rather developmental. Furthermore, since the expression of LTα in the thymus correlates with that of Foxp3, which dictates Treg cell identity, this suggests that Tregs express key molecules that tightly control their activity to prevent the cell to over-react and thus over-suppress immune reactions.

Both thymic and splenic LTα$^{-/-}$ Tregs do not show any obvious defect in the expression of CD39, CD73 and CD25 implicated in metabolic disruption and of CTLA-4 and LAG-3 implicated in the modulation of antigen presentation. In contrast, they show increased expression of IL-10, TGF-β and IL-35 immunosuppressive cytokines and granzyme B, IFN-γ and FasL involved in cytotoxicity-mediated suppression mechanisms. Although further investigations are required to define precisely their suppressive mode of actions, our results nevertheless indicate that LTα$^{-/-}$ Tregs likely mediate their potent suppressive activity through the secretion of inhibitory cytokines and the expression of molecules involved in cytolysis of target cells. RNA-seq data confirmed that LTα$^{-/-}$ Tregs show an activated/effector phenotype, characterized by augmented expression of Blimp-1, Klrg1 and Tigit markers, described to distinguish terminally activated and/or differentiated effector Tregs. Consistently with these observations, higher frequencies of CD44$^{hi}$CD69$^+$ and KLRG1$^+$ effector Treg cells were also observed in the spleen of LTα$^{-/-}$ mice by flow cytometry. LTα$^{-/-}$ Tregs also express high levels of the Ikaros family transcription factor, Helios. Interestingly, CD4$^+$Foxp3$^+$Helios$^+$ Tregs have been shown to possess a highly suppressive function within the bulk of CD4$^+$CD25$^+$ Treg population. Furthermore, forced expression of Helios enhances the suppressive function of Tregs whereas Helios knock-down results in decreased of the suppressive function both in vitro and in vivo. This high expression of Helios thus comforts the notion that LTα$^{-/-}$ Tregs are highly immunosuppressive. Splenic LTα$^{-/-}$ Tregs also express higher level of Nur77, which is an immediate early gene upregulated by TCR stimulation, suggesting that they were recently activated by antigens. Furthermore, RNA-seq data revealed that LTα$^{-/-}$ Tregs show a signature of highly proliferative cells, which was confirmed by high frequencies of Ki-67$^+$ proliferative Treg cells by flow cytometry. Altogether, these data show that LTα$^{-/-}$ Tregs possess an activated/effector phenotype.

Although the stability of the Treg phenotype is a debated issue, we observed that adoptively transferred LTα$^{-/-}$ Tregs retained their highly immunosuppressive signature in vivo at least 7 days after transfer. The stability of LTα$^{-/-}$ Treg phenotype suggests that the transfer of these suppressive cells could show benefits in pathological conditions. Given that LTα$^{-/-}$ Tregs show a highly immunosuppressive signature, we have evaluated whether the adoptive transfer of LTα$^{-/-}$ Tregs displays superior therapeutic benefits than WT Tregs in protecting and treating inflammatory bowel disorders. Interestingly, the transfer of LTα$^{-/-}$ Tregs protects from DSS-induced colitis and treats from IBD more efficiently than WT Tregs. This was reflected by a reduced body weight loss, a higher colon length and a reduced histological score in mice transferred with LTα$^{-/-}$ Tregs compared to mice injected with WT Tregs. Furthermore, we observed that LTα$^{-/-}$ Tregs substantially reduce colon inflammation and the infiltration of inflammatory immune cells. In the DSS-induced colitis model, we found that the transfer of LTα$^{-/-}$ Tregs before the induction of colitis reduces the priming and/or expansion of Th1 and Th17 pathogenic cells in mesenteric lymph nodes. Importantly, the ratios Treg/Th1 and Treg/Th17 were increased in the colon in both the DSS-induced colitis and IBD models, suggesting that Tregs can also exert their suppressive effects locally in this tissue.

By their ability to suppress colon inflammation, the adoptive transfer of LTα$^{-/-}$ Tregs also attenuates the development of CAC, which is known to be promoted by chronic inflammation. This was illustrated from colon carcinogenesis at ~6 weeks by a ~3-fold reduction in numbers of colorectal tumors that showed smaller volumes than tumors from mice injected with WT Tregs. Importantly, this protective effect persisted until the end of the CAC protocol i.e. at −12 weeks even if it was less pronounced. Compared to mice transferred with WT Tregs, this attenuation in CAC development in mice that received LTα$^{-/-}$ Tregs is explained by a reduced colon inflammation observable from 3 weeks of the CAC protocol. This was characterized by a reduced (i) colon weight/length ratio, (ii) expression of pro-inflammatory cytokines and (iii) chemokines implicated in the recruitment of inflammatory immune cells into the colon. Altogether, these data indicate that compared to their WT counterparts, LTα$^{-/-}$ Tregs show a higher capacity to treat colitis and protect from both colitis and CAC development. LTα$^{-/-}$ Tregs thus show an augmented anti-inflammatory/immunosuppressive function than WT Tregs. By decreasing the number of adoptively transferred cells, we were able to determine that Ltα$^{-/-}$ Tregs are −4 times more suppressive in vivo than their WT counterparts.

Importantly, mixed bone marrow chimeras showed that the activated/effector phenotype of LTα$^{-/-}$ Tregs is due to the specific loss of LTα expression in hematopoietic cells and likely not in non-hematopoietic stromal cells. Furthermore, our data revealed that LTα1β2/LTβR interactions between Tregs and dendritic cells, particularly Sirpα$^+$ cDCs and pDCs, negatively control the suppressive signature of Treg cells, suggesting that a direct cell contact with antigen-present cells regulates Treg suppressive activity.

Since LTα, expressed as a membrane anchored LTα1β2 heterocomplex, is conserved in human Tregs, the adoptive transfer of LTα$^{-/-}$ Tregs is expected to find therapeutic applications to prevent and/or treat other inflammatory and autoimmune disorders. Furthermore, the transfer of these cells could also be beneficial to protect from the development of other inflammation-induced cancers such as pancreatic, lung or bladder carcinoma, induced by chronic pancreatitis, bronchitis and cystitis, respectively.

In conclusion, our study identified that LTα expression in Tregs fine-tunes the suppressive capacity of this cell type. LTα could thus represent an interesting new therapeutic target to increase Treg activity, which is expected to find clinical applications in the field of Treg cell therapy by reducing the required cell number and by efficiently treating inflammatory and autoimmune disorders and preventing the development of inflammation-induced cancers.

REFERENCES

Throughout this application, various references describe the state of the art to which this invention pertains. The disclosures of these references are hereby incorporated by reference into the present disclosure.

The invention claimed is:
1. A method of treating inflammatory bowel disease in a subject in need thereof comprising administering to the subject a therapeutically effective amount of a population of regulatory T cells, wherein the population of regulatory T cells is genetically modified so that it does not express or expresses reduced levels of lymphotoxin alpha, wherein the regulatory T cells are genetically modified to silence a lymphotoxin alpha gene.

2. The method according to claim 1, wherein the regulatory T cells express a chimeric antigen receptor which recognizes and/or binds to an autoantigen.

* * * * *